(12) United States Patent
Boots et al.

(10) Patent No.: US 8,177,549 B2
(45) Date of Patent: May 15, 2012

(54) METHOD AND APPARATUS FOR PROCESSING OF MATERIALS

(76) Inventors: Craig Gordon Boots, Madisonville, LA (US); Robert D. Bartlett, New Orleans, LA (US); Ryan J. Bright, New Orleans, LA (US); Mark C. Woodin, New Orleans, LA (US)

(*) Notice: Subject to any disclaimer, the term of this patent is extended or adjusted under 35 U.S.C. 154(b) by 912 days.

(21) Appl. No.: 12/094,622

(22) PCT Filed: Dec. 5, 2006

(86) PCT No.: PCT/US2006/061604
§ 371 (c)(1),
(2), (4) Date: Sep. 15, 2008

(87) PCT Pub. No.: WO2007/117313
PCT Pub. Date: Oct. 18, 2007

(65) Prior Publication Data
US 2009/0215000 A1    Aug. 27, 2009

Related U.S. Application Data

(60) Provisional application No. 60/742,824, filed on Dec. 5, 2005.

(51) Int. Cl.
*F27B 7/14* (2006.01)

(52) U.S. Cl. .................. 432/118; 432/108; 366/227

(58) Field of Classification Search .................. 432/103, 432/105, 108, 118; 241/181, 183; 366/222, 366/227
See application file for complete search history.

(56) References Cited

U.S. PATENT DOCUMENTS

| | | | | |
|---|---|---|---|---|
| 2,084,713 A * | 6/1937 | Thayer | | 432/107 |
| 2,207,987 A * | 7/1940 | Wetherald et al. | | 432/114 |
| 4,403,952 A * | 9/1983 | Birch et al. | | 432/103 |
| 4,674,691 A * | 6/1987 | Didion | | 241/8 |
| 4,776,788 A * | 10/1988 | Przewalski | | 432/103 |
| 4,974,781 A | 12/1990 | Placzek | | |
| 4,988,289 A * | 1/1991 | Coucher | | 432/103 |
| 5,119,994 A | 6/1992 | Placzek | | |
| 5,746,987 A | 5/1998 | Aulbaugh et al. | | |
| 6,803,017 B2 * | 10/2004 | Bertolotti et al. | | 266/213 |
| 7,575,043 B2 * | 8/2009 | Kauppila et al. | | 165/47 |

FOREIGN PATENT DOCUMENTS

| | | |
|---|---|---|
| DE | 90 00 530 | 3/1990 |
| FR | 871 651 | 5/1942 |
| GB | 203 673 | 5/1924 |
| WO | WO 2004/070300 | 8/2004 |

* cited by examiner

*Primary Examiner* — Gregory A Wilson
(74) *Attorney, Agent, or Firm* — Garvey, Smith, Nehrbass & North, L.L.C.; Brett A. North

(57) ABSTRACT

A method and apparatus processing materials including medical waste, municipal waste, along with other wastes, and processing materials; the apparatus comprising an elongate pressure vessel of generally cylindrical configuration having an inlet end, and an end cap for the inlet.

30 Claims, 23 Drawing Sheets

METHOD AND APPARATUS FOR PROCESSING OF MATERIALS

CROSS-REFERENCE TO RELATED APPLICATIONS

U.S. Provisional Patent Application Ser. No. 60/742,824, filed 5 Dec. 2005 is incorporated herein by reference.

Priority is hereby claimed to U.S. Provisional Patent Application Ser. No. 60/742,824, filed 5 Dec. 2005.

STATEMENT REGARDING FEDERALLY SPONSORED RESEARCH OR DEVELOPMENT

Not applicable

REFERENCE TO A "MICROFICHE APPENDIX"

Not applicable

BACKGROUND

U.S. Pat. Nos. 5,119,994 and 4,974,781 are incorporated herein by reference.

Rising concerns regarding proper handling and disposal of waste materials continues to occur. One serious waste disposal problem is that of medical waste materials that can harbor infectious agents and diseases. Incidents of medical waste materials washing ashore along the coastlines and of bags of medical waste materials being dumped in ditches strike fear into the hearts of all people, causing an outcry for better controls.

Public opinion has caused activity by legislators and regulators, particularly at the federal level, concerning the management of medical wastes. The Environmental Protection Agency (EPA), the Office of Technology Assessment (OTA), the Center for Disease Control (CDC) and the Occupational, Safety and Health Act (OSHA) have issued management guidelines and regulations regarding medical wastes including the Medical Waste Tracking Act.

Medical wastes that potentially harbor infectious agents have been identified by the OTA as being generated by hospitals, clinics, doctor's offices, dentist's offices, veterinarian's offices, mortuaries, laboratories and other medical and research facilities. Recognized options for handling and managing these wastes include incineration, microwaving, autoclaving, chemical treatment, hydropulping and land disposal. A large percentage of hospital generators in the United States use or have access to some type of combustion system to incinerate these wastes.

Combustion of medical wastes has the unfortunate effect of releasing pollutants into the air. Of primary concern is the release to the atmosphere, from the medical waste combustors, the pollutants of hydrogen chloride (HCl), sulfur dioxide ($SO_2$), particulate matter (PM), trace organics such as dioxins and furans, arsenic (As), cadmium (Cd), chromium (Cr), mercury (Hg), lead (Pb), and others. Many of the combustion systems that are in service do not adequately control these pollutants and are a cause for concern. This concern has been addressed by Section III of the Clean Air Act (CAA), and these regulatory standards may preclude the use of medical waste combustion at many installations by requiring extensive control measure to be added to combustion facilities.

Medical waste generation rates have increased substantially in the past twenty years. The increase is believed due to factors such as the increasing use of disposable materials and the redefinition of the regulated waste fraction. As diseases such as AIDS receive increasing public attention, increasing pressure will be brought to bear on the generators of medical waste to the extent that anything that comes into contact with a patient or a patient's blood or bodily fluids will be classified and managed as being potentially infectious. This circumstance is called "Universal Precautions" by the CDC.

With such circumstances developing, hospital administrators attempt to balance their systems to minimize medical waste amounts that are potentially infectious and that are the most costly to manage, by having their staff segregate wastes in multiple containers within hospital rooms and operating rooms. This can lead to arbitrary decisions as to what is infectious and what is not, and places an additional burden upon a staff that often works under crisis conditions. The concern, of course, is that incorrectly classified material may be incorrectly disposed of. Incorrect disposal could result in violations of the regulations for management of these wastes with severe fines being levied on the violator or, in the worst case, be the cause of an outbreak of an infectious agent functioning to contaminate people. However, to practice no segregation of materials and to classify all waste as potentially infectious would be economically prohibitive to a generator.

In light of this growing dilemma, it has become appropriate to strive for the perfection of a method and an apparatus for the processing of medical wastes into ordinary, common wastes so that these wastes may then be managed for disposal or recycling in the commonly accepted general waste disposal system without the threat of the spread of an infectious agent.

Waste paper has been recycled and used as a source of feedstock for the manufacture of paper products. The availability of recycled paper, however, is subject to the economics of the recovery, sorting, and cleaning of the waste paper from the waste paper containing materials requiring sorting of the paper at the source of generation and special handling by the generator; dedicated pickup of specially segregated materials by a recycler; and component separation by the recycler after collection.

Waste plastics have become increasingly important because of their very long term resistance to degradation and decomposition in the environment and because of the hazardous nature of the gaseous compounds that are produced when plastics are incinerated. The recovery, sorting, and cleaning of waste plastics for recycling, as with waste paper, typically also requires sorting of the plastic at the source of generation and dedicated pickup of specific plastics by a recycler to be viable as a source of plastic to be utilized by the plastics industry.

It has long been recognized that the achieving of a method of separating waste paper and plastics from the extraneous contaminating components that typically accompany a paper containing waste material would be highly desirable. This is particularly true if the paper and plastic containing waste material is municipal solid waste. Municipal solid waste typically contains 25-60% paper materials along with a varying assortment of glass, metals, rags, food wastes, plastics, etc. It is believed that typical component compositions for municipal solid wastes are as follows:

TABLE 1

| | |
|---|---|
| Paper | 35.2% |
| Metals | 8.0% |
| Plastic | 11.3% |
| Glass | 5.3% |
| Food Waste | 11.7% |
| Grass Clippings | 12.1% |

TABLE 1-continued

| | |
|---|---|
| Wood | 5.8% |
| Leather, Textiles, and Rubber | 7.4% |
| Other | 3.4% |
| TOTAL | 100.0% |

It is believed that much paper and plastic containing waste materials are being landfilled, resulting in the loss of paper and recyclable materials and the using up of valuable land space. Landfills also threaten the environment with contamination of surface and groundwater, and present health hazards and public nuisances by increasing numbers of disease-carrying birds, rodents and insects. The problem is an ever-increasing one. By their existence, municipalities and industries generate paper-containing and plastic-containing wastes continually and these wastes must be properly disposed of. Various approaches such as incineration, composting, and producing refuse-derived fuel have been considered as alternative solutions to landfills.

Incineration, although it can reduce the amount of landfilling required, produces undesirable and hazardous pollutants released in the air, primarily by the combustion of plastics contained in the waste materials and the volatilizing of metals such as aluminum contained therein. Incineration also produces relatively few products generating revenue except for energy sales of steam and electricity, which are dependent on adjacent customers and subject to rates set by local public utilities, causing most of the costs related to incineration facilities to fall on the public attempting to deal with the waste streams.

Composting, which is the process of subjecting waste materials to microbial action to produce a soil-like material is believed to have potential only as a soil conditioner. Because it contains relatively little nutrient value, compost cannot compete as a fertilizer. Additionally, the concentration of heavy metals in compost may be unacceptable considering that these will be absorbed into plants, and up the food chain.

Producing refuse-derived fuel from waste materials requires that a series of steps be taken to separate combustible materials from non-combustible materials. Separation results in several classification processes, producing a number of low quality products of limited value. The refuse-derived fuel produced contains plastics which produce undesirable and hazardous pollutants released to the atmosphere when combusted.

Because of problems inherent in present methods of waste disposal, the continuing need to dispose of waste materials, and the need to recover valuable products currently being lost, there is a need to provide improved methods of separation and recovery of component fractions from waste paper and plastic containing materials.

While certain novel features of this invention shown and described below are pointed out in the annexed claims, the invention is not intended to be limited to the details specified, since a person of ordinary skill in the relevant art will understand that various omissions, modifications, substitutions and changes in the forms and details of the device illustrated and in its operation may be made without departing in any way from the spirit of the present invention. No feature of the invention is critical or essential unless it is expressly stated as being "critical" or "essential."

SUMMARY

"Pulpable materials" mean those materials that when subjected to heat, moisture or agitation or any combination of those reduces to a pulpy mass.

"Recycled Paper" means all of those materials that consist of the product of cellulosic fibers that have been reduced to pulp and reconstructed into containers, wrappers, or materials to write on.

"Plastic" means organic, synthetic or processed materials including resins, foams, films, sheets and alloys (composites) that are molded, cast, extruded, drawn or laminated into objects or films.

"Medical waste" means waste that potentially contains pathogens with sufficient virulence and quantity so that exposure to the waste by a human host could result in an infectious disease.

"Red Bag" means the red colored, plastic bag that is required by regulation to be used as the container for infectious waste materials.

A condition known to those skilled in the art as "segregation" occurs in a rotating drum processing non-homogeneous and variable sized materials. "Segregation" is the phenomenon in which a rotating drum causes materials of different size and density to separate and stratify according to size and density, with the smallest, most dense particles migrating to the bottom of the mass of materials and the largest and lowest density particles rising to the top of the mass of materials in the rotating drum, with layers of intermediate sized and dense particles being sandwiched between them. The result of "segregation" is that the particles in the middle of the mass of materials can be insulated from the reactive environment of the drum, and not be adequately sterilized.

One embodiment provides a method and an apparatus that accomplishes the sterilization of medical waste materials by contact with a sterilizing agent transforming the medical waste materials into ordinary, common waste materials having approximately one third of their original volume, accomplished by the use of buckets along the interior of an elongate drum rotationally disposed within a pressure vessel. These components effect a high degree of agitation of materials, facilitating the contacting of the materials with the sterilizing agent.

One embodiment allows medical waste materials to be processed be handled and introduced into the apparatus without it being necessary beforehand to be size reduced, separated or removed from its protective Red Bag or container.

One embodiment includes the introduction of waste material introduced into a processor, the interior of which is equipped with a rotatable cylindrically configured drum. The interior of the drum can be equipped with a series of upsets or buckets and directional helical flighting that, by virtue of their configurations, cause a high degree of agitation of the materials to be processed when the drum is rotated. The waste introduced into the processor in its undisturbed bags can be agitated by rotating the interior cylindrical drum. The waste can be treated by the addition of substantial heat during agitation of the medical waste within the processor. The addition of heat into the processor causes the bags to become softened and distorted and, in combination with agitation by the upsets or buckets along with the helical flighting, causes the bags to be opened spilling their contents into the interior of the processor. The waste material can be treated with added moisture and/or heat while agitation of the waste materials continues.

In one embodiment as the process continues, contacting of the materials with the added moisture in conjunction with agitation causes the moisture absorbable materials to break down into their repulped form causing a significant reduction of the overall volume of the waste materials.

In one embodiment the processing of waste materials can continue with the addition of more heat sufficient to sterilize the now-exposed medical waste materials. The waste materials being processed can be held at a temperature of at least 275° F. (135° F.) for a period of at least 15 minutes, at a pressure of approximately 50 psig (345 kilopascals), or other combinations of pressure, temperature and time as have been proven to accomplish complete and effective sterilization of the waste materials.

In one embodiment adding moisture increases transfer of heat into the waste materials being processed, compared to a "dry treatment" state which can produce an insulating effect for at least pockets of the waste materials being treated, avoids creation of pockets in which infectious materials can be protected from sufficient heat to accomplish adequate sterilization.

In one embodiment, because of the reduction in size of repulpable fractions of the medical wastes (as they are processed), and because heat added during treatment causes plastic fractions to become heat distorted and to collapse into more compact forms; the entire amount of the waste is more completely agitated and therefore most completely contacted by the sterilizing heat.

In one embodiment after the waste materials have been processed for a sufficient amount of time at a sufficiently high temperature, a vacuum can be induced to extract excess moisture from the processed materials. Subsequently, the resultant processed material does not drain water during disposal and has a lower density when compared to processed materials not subject to dewatering. The extracted water can be recovered and held for reuse in processing additional waste materials.

In one embodiment instead of using high temperatures to sterilize the medical wastes, after the wastes have been spilled into the interior of the processor, a sterilizing chemical such as sodium hypochlorite or an equivalent chemical agent can be added to the processor as a part of the necessary moisture to accomplish repulping and in sufficient quantities to effect sterilization and by this addition, medical wastes can also be effectively treated.

In one embodiment, instead of using a vacuum system to accomplish dewatering of the processed waste materials, a mechanical dewatering system such as a dewatering press of the type that is commercially available from the Somat Corporation could be used.

In one embodiment the materials can be discharged from the processor for the recovery of the sterilized materials for recycling, or the sterilized materials can be subjected to grinding or other size reduction techniques so as to destroy the integrity of such materials as needles and other "sharps" that are otherwise unaffected by the processing, and render them physically harmless as well as pathologically harmless.

One embodiment includes a generally cylindrical vessel mounted at a slight angle of incline with respect to the horizontal, with the preferred angle of incline being about 7 degrees, the upper end of the vessel having an opening to receive materials and the lower end of the vessel being closed. The vessel can have an end cap sealing the vessel from the atmosphere thereby allowing a buildup of pressure during operation, or, alternatively, permitting a vacuum to be maintained within the vessel by use of a vacuum system.

One embodiment has the vessel equipped with a generally cylindrical drum located inside the shell of the vessel mounted on bearings allowing rotation of the drum inside of the vessel around its horizontal axis selectively in either direction. The upper end of the drum can have an opening to receive materials to be processed, whereas the lower end of the drum can be closed and watertight. The drum can be equipped with upsets or buckets and helical flighting located on its interior, to facilitate agitation of material placed therein and to direct movement of the materials within the drum.

In one embodiment, as the drum is rotated, the materials in the drum are tumbled in contact with the sidewall of the drum, a distance equal to the angle of repose of the materials times the coefficient of friction of the materials times the rate of rotation of the drum. The angle of repose of the medical waste is approximately 45 degrees and the coefficient of friction is approximately 0.2. As the drum continues to rotate past the maximum point of the angle of repose of the materials, the materials are tumbled from the sidewall of the drum down upon itself. The angle of incline of the drum facilitates movement of the materials through the drum in that at the point of the angle of repose of the materials, the material is tumbled upon itself a distance equal to the sine of the angle of incline of the drum times the height of the material on the sidewall of the drum and in a direction concurrent with the downward slope of the angle of incline. The angle of incline also contains the material being processed in the interior of the rotating drum by virtue of the material being directed away from the opening of the drum as a consequence of the movement of the material by the rotation of the drum.

One embodiment overcomes "segregation" and compaction against the rear of the drum through use of upsets or buckets at various locations on the interior of the drum. The buckets can be attached to the interior perimeter to avoid appurtenances within the drum restricting flow or entangling materials. The movement of materials within the drum by the buckets can occur in concert with the rotation of the drum along with movement caused by the drum's angle of incline. Materials can be lifted by each bucket in concert with the rotation of the drum and then discharged as drum rotation continues. Such a process tends to prevent segregation by causing thorough agitation of the materials being processed.

In one embodiment movement of materials within the drum can also be accomplished by helical flighting causing longitudinal motion of material contacted by the helix. The direction of movement of material from the helix is dependent upon the direction of rotation of the drum; one rotative direction causing forward movement through the drum away from the inlet end and a second rotative direction causing backward movement toward the inlet end of the drum.

In one embodiment agitation of the materials can be accomplished by directional helical flighting and tumbling of materials during the rotation of the drum as the materials are contacted by the face of the helix. Longitudinal movement of the materials through the drum can be accomplished by the angular nature of the helix (e.g., pitch of the helix or helical faces) in combination with rotation of the drum. The helix can be connected to the interior perimeter of the drum in an unbroken form, and can be configured to avoid appurtenances within the drum that would prohibit material flow or that might entangle materials. In one embodiment, as may be apparent to those skilled in the art, the rate of movement of materials by the helical flighting within the drum is dependent upon the depth of the helix, the frequency of the helix and the rate of rotation of the drum. These variables are a function of the amount of material to be processed in a given amount of time.

In one embodiment a nested helix is used for at least part of the length of the drum. In one embodiment two, three, four, or more nested helixes are used. The advantage of nesting is to increase the amount of movement of material per rotation of the drum. In one embodiment the nesting occurs only part of the length of the drum.

In one embodiment medical waste material, in its undisturbed red bag containers, can be introduced into the drum while the drum is being rotated in the first rotative direction to facilitate filling of the drum. After the desired quantity of waste is placed in the processor, the end cap can be closed and the waste processed with added moisture and heat while the drum continues to rotate in the first rotative direction. During the processing of the medical waste materials, the interaction of the forward movement of materials through the drum by the helical flighting, the angle of incline, and the movement of the materials by the buckets results in thorough mixing and, therefore, increased contacting of materials with added moisture and heat for sterilization.

In one embodiment, after processing is completed, the end cap can be opened and the drum rotated in the second rotative direction. The backward movement of materials by the helical flighting in this second rotative direction can empty the processor of the processed materials. In one embodiment an apparatus for processing medical waste materials comprises be an elongated pressure vessel of generally cylindrical configuration having an inlet end and an end cap. Contained in the vessel can an elongate drum of generally cylindrical configuration, mounted for rotation about its longitudinal axis, and having means for selectively driving it in two rotative directions about the longitudinal axis. The drum can have an inlet end corresponding with the inlet end of the vessel, with the longitudinal axis of the drum being at an angle of incline to the horizontal, and the inlet end higher than its opposite end, which is closed and watertight.

In one embodiment means are provided for agitating the medical waste within the drum by non-obstructive, helically configured means mounted at spaced locations along the interior perimeter of the drum, such that, during rotation of the drum in a first rotative direction, the helically configured means intercepts the waste materials and tends to move same forward, in the direction away from the inlet, toward the closed end of the drum, whereas during rotation of the drum in the second rotative direction, the helically configured means intercepts the waste materials and tends to move same backward in the direction toward the inlet end of the drum.

One embodiment provides a means for adding controlled amounts of moisture to the interior of the vessel during drum rotation, to enhance the penetration of beat into the moisture absorptive materials of the waste materials, thereby enhancing the effort involved in bringing about sterilization.

One embodiment provides several devices affixed to the vessel, such as water piping, steam piping, vacuum piping, pressure controllers and other instruments for monitoring the process in one embodiment controllers and monitors are affixed to the shell of the vessel at locations that are nearer to the reactive environment center of the process, regardless of the rotation of the drum within the vessel.

In one embodiment, because the drum is open on one end, the drum experiences the same conditions of pressure, temperature, and vacuum seen in the pressure vessel. Water and steam can be injected into the opening of the drum by piping that is permanently fixed and supported to intrude into the opening of the drum without having to touch the drum.

In one embodiment the drum can be inclined at a slight angle to the horizontal and the lower end of the drum is closed and watertight. The upper end of the drum can be open and through this open end water, steam, and other materials can be added. The amount of water to be added corresponds to the amount of material that is to be processed. The water will tend to accumulate at the lower end of the drum.

One embodiment provides independent heating of inner drum by such means as being a double wall jacket with steam, hot oil, or some other heating medium piped through pipes routed through a hollow drive shaft. Alternatively, the drum could be heated by radiant heat transfer by such means as heated tubes or electrically heated elements in the annular space between the inner drum and shell, or convective heat transfer or a combination of the two. In one embodiment heat is used to at least partially dry the drums contents either with or without the use of a reduced total pressure or reduced partial pressure of the evaporating component to accelerate evaporation, or to cause evaporation at a temperature that would be advantageous because it would be lower or because it could cause selective evaporation primarily of one or several components.

In one embodiment the drive shaft can be cantilevered.

In one embodiment one or more of the roller shafts can be cantilevered.

In one embodiment a hollow drive shaft can be used permitting the admission of a purging gas to allow, for example, the reduction of air in the vessel prior to processing by purging with steam. This allows the reduction in the partial pressure of non-condensibles (e.g., air) without requiring that a high vacuum be obtained. Connection to the pipes in the shaft could be through a commercially available rotary joint familiar to those skilled in the art.

In one embodiment buckets or upsets can cause an increased agitation of materials in the drum. In one embodiment the buckets are staggered from each other from section to section. This effective positioning of the buckets can also cause a more even loading of forces on the drive and support mechanisms of the drum by virtue of the more even lifting of the materials by the buckets.

In one embodiment the diameter of the drum is sufficient to accept a bag of material to be processed with an additional space of approximately 40% of the volume of the interior diameter of the drum left vacant to allow materials to fall and to mix within the drum as it rotates. Additional processing capacity can be added to the processor by increasing its length. The ratio of diameter to length is variable and depends upon the amount of material to be processed in a given amount of time in concert with the size and frequency of the agitation mechanisms of the drum to insure complete mixing of materials.

In one embodiment the pressure vessel can be supported by structural steel supports designed to transfer the weight of the processor and its contained materials to the foundation under the processor, which foundation has a sufficiently wide base to give the vessel stability. The rotating drum within the shell of the vessel will transfer its forces to the carrier and support bearings which in turn will transfer that load into the shell of the vessel and become a part of the load supported by the structural supports of the shell and transferred to the foundation below the processor.

In one embodiment a method and an apparatus for the separation and the recovery of component fractions, especially paper and plastic, from paper-containing and plastic-containing waste materials. In one embodiment paper and plastic containing waste materials can be handled and introduced into the apparatus without prior size reduction, or separation and special handling of waste. In one embodiment is necessary to remove from the waste stream, certain items such as large appliances, demolition rubble, etc.

In one embodiment paper-containing and plastic-containing waste material can be initially treated with moisture to achieve a minimum moisture content of 30% in the moisture absorptive materials by weight, with 65% to 80% moisture content of the moisture absorptive materials by weight being optimum. The moisture non-absorptive materials, such as metals, glass and plastics that may be present are ignored in the moisture addition calculations. The apparatus is then agitated by suitable means well known to those skilled in the art, in this case by rotation to accomplish agitation of the mixture to allow the moisture to have complete and intimate contact with the components in the waste material, thus to effect repulping of the paper components. Heat may be applied to the mixture in the form of hot water that is added to achieve the desired moisture content, or by heat exchangers in the shell of the apparatus or installed inside the apparatus. Preferably, however, heat in the form of saturated steam is injected directly into the mixture. The addition of heat to a reaction, increases the rate of the reaction.

In one embodiment repulping can be accomplished in the presence of moisture, and agitation and the time of repulping is affected by the appropriate addition of heat. This results in a size reduction of the various and irregularly sized paper components in the mixture into a homogeneous pulp, and a corresponding increase in the bulk density of those pulped components that are able to be separated from the non-pulpable components in the mixture. Various components such as food wastes that are pulpable are partially hydrolyzed and pulped, and are incorporated into the pulped fluff of the paper components.

In one embodiment after repulping has been accomplished, the apparatus can be rotated to empty the vessel of pulpable components and non-pulpable components, and these separated components directed to classification equipment. Such classification equipment preferably includes trommels, magnetic separators, flotation chambers and sorting tables effective to recover product streams. Additional methods of classification are known to those skilled in the art.

In one embodiment as the repulping is accomplished, the volume of materials is condensed to approximately one-third of the initial volume of the materials and as the repulping process is being conducted, an increasing percentage of the materials is being directed "backward" through the vessel. The amount of mixing of the materials by the helix can be dependent on the frequency of the helix in that a greater frequency, that is, more complete helical cycles per revolution of the drum, results in more helical surface area in contact with the material in the drum and therefore more movement of material within the mass of material in the drum.

It is well known to those knowledgeable in the industry that a segregation by size of materials occurs in a rotating drum with the larger particles (non-pulped materials) rising to the top of the mas of materials in the drum and the smaller particles (pulped materials) falling to the bottom of the mass of materials.

In one embodiment the action of the helix can cause an amount of material at the bottom of the drum equal to the depth of the helix to be conveyed through the mass of materials. Because size segregation will occur tend to occur in the helix, upon rotation of the drum in the first rotative direction to discharge the materials from the drum, the pulped materials which have fallen to the bottom of the mass of materials can be conveyed through the mass of materials and discharged, at least to some extent, first. The non-pulped materials, which have risen to the top of the mass of materials due to the effect of segregation, will, at least to some extent, be discharged last.

In one embodiment the drum can be rotated in the second rotative direction, that is, the direction that accomplishes movement by the directional flighting of the contained materials backward through the drum, during the time that heat is added to the material in the form of saturated steam. This is to further enhance the contact of the mixture of materials with the added heat, and it should be noted that the amount of steam added to the mixture of materials is determined by the amount of material to be processed in a prescribed amount of time.

In one embodiment the apparatus can be equipped with a well-known type of positive feeding device for forcing the non-flowing materials to be treated, such as positive feeding device like a hydraulic or pneumatic ram.

In one embodiment the apparatus is equipped with piping to facilitate the addition of moisture to the necessary concentration of the mixture of the materials, and the addition of heat to increase the rate of reaction. Furthermore, pressure relief vents can direct the residual heat of the process to heat exchangers for energy conservation and for safety of operations.

In one embodiment is provided a method and apparatus for accepting substantially untreated paper-containing and plastic-containing waste material and, in a single unit operation, to accomplish repulping of the pulpable components in the waste material, thus to produce a homogeneous pulped product that separates readily from the non-pulpable components included in the waste material.

In one embodiment is provided a method for considerably reducing the bulk of waste material, by accomplishing a thorough mixing of such waste material in the presence of heat and agitation, with this method being able to be pursued without necessitating the employment of highly skilled personnel.

DETAILED DESCRIPTION

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate system, structure or manner.

Figure 1:
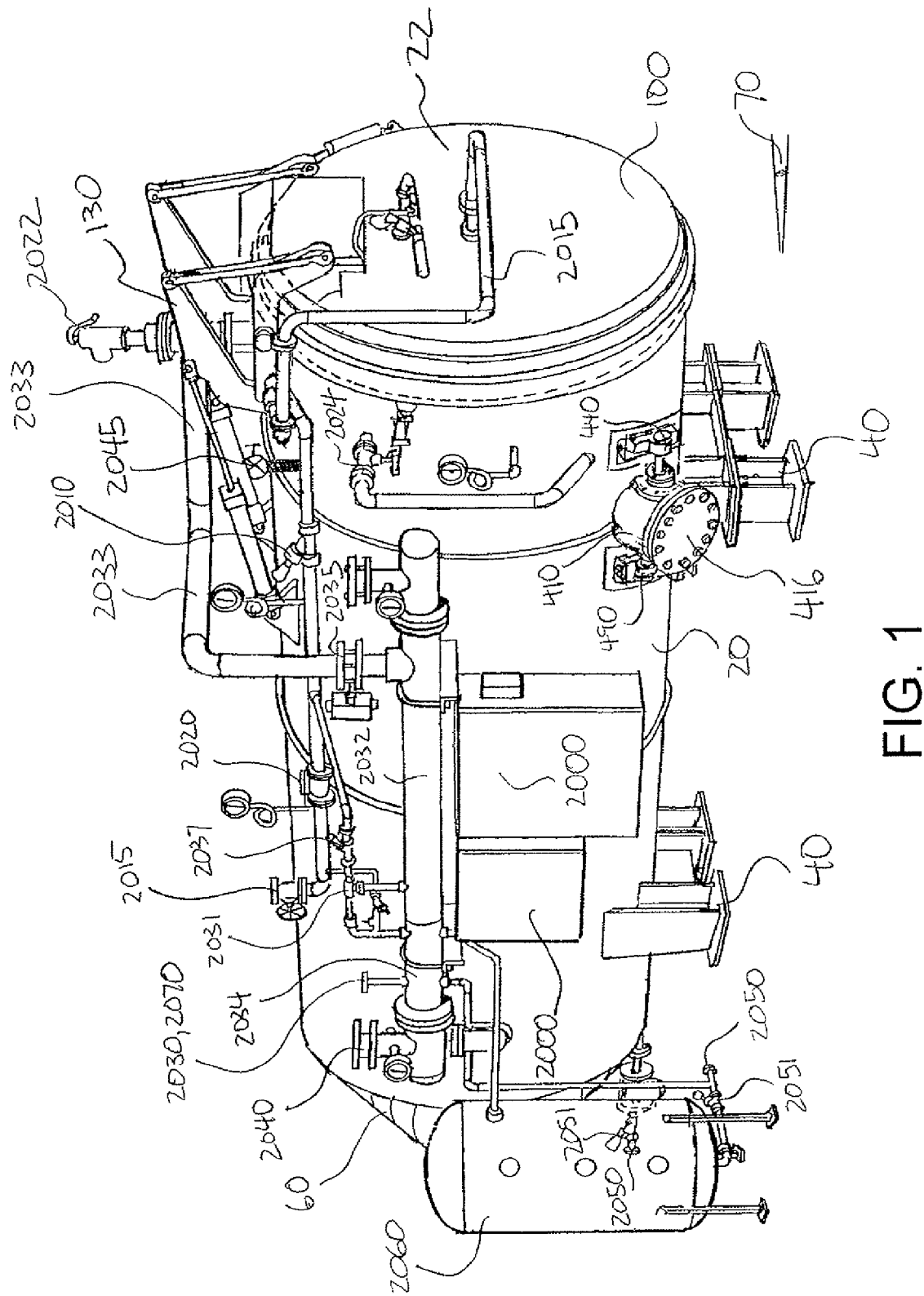
FIG. 1 is a perspective view of the exterior of one embodiment of a pressure vessel for treating materials.
Figure 2:
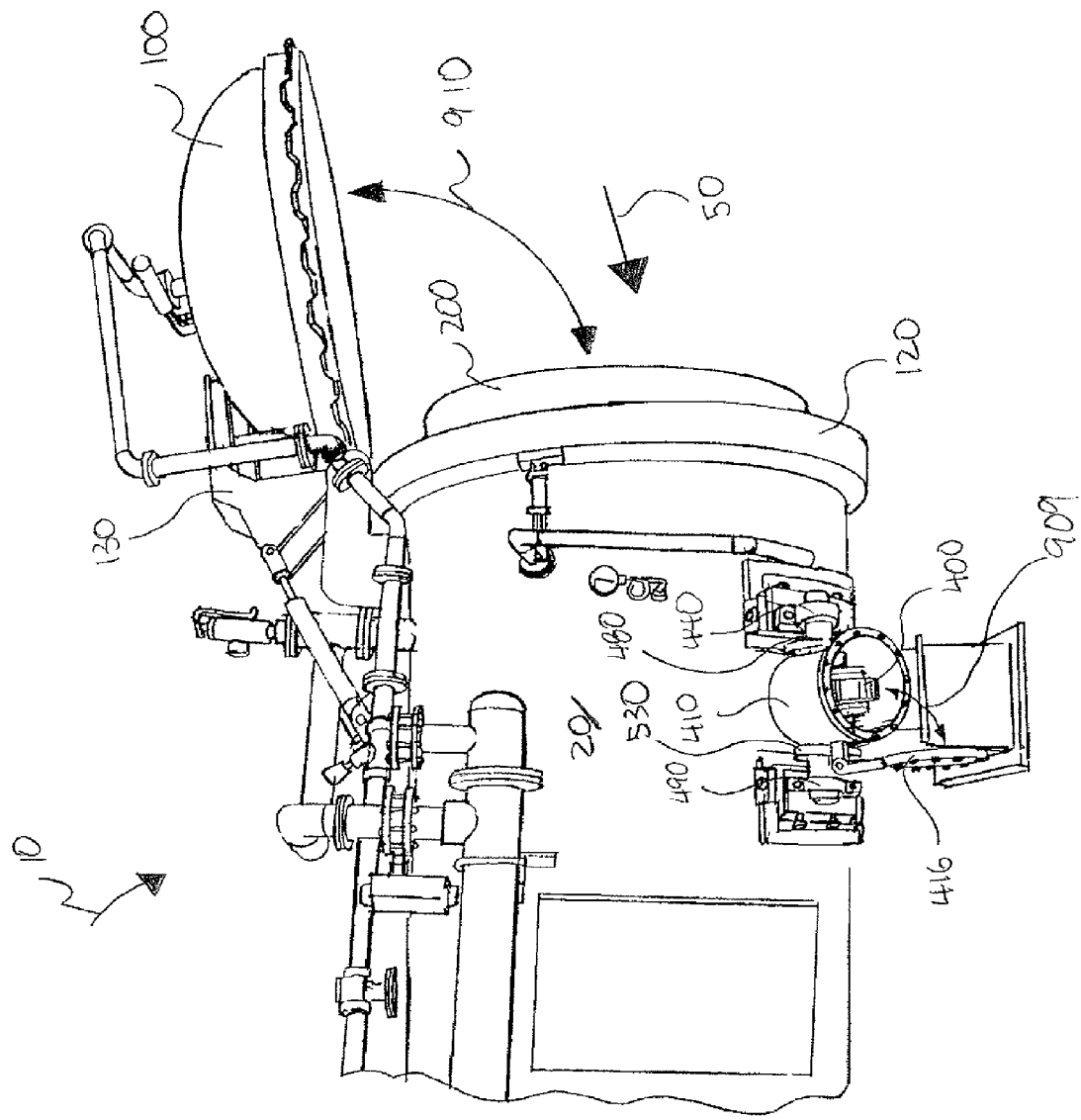
FIG. 2 is a perspective view the vessel of FIG. 1 with the end cap opened.
Figure 3:
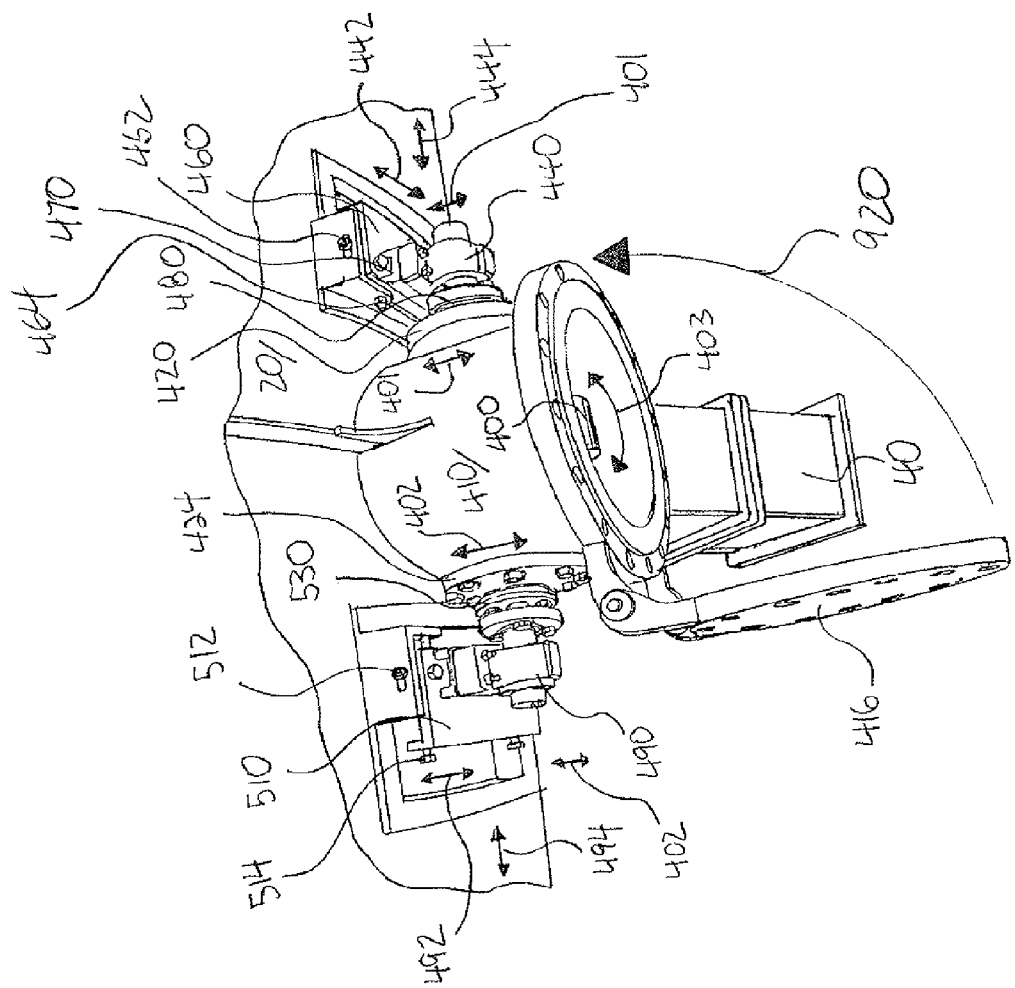
FIG. 3 is a perspective view of a roller housing with plate opened.
Figure 4:
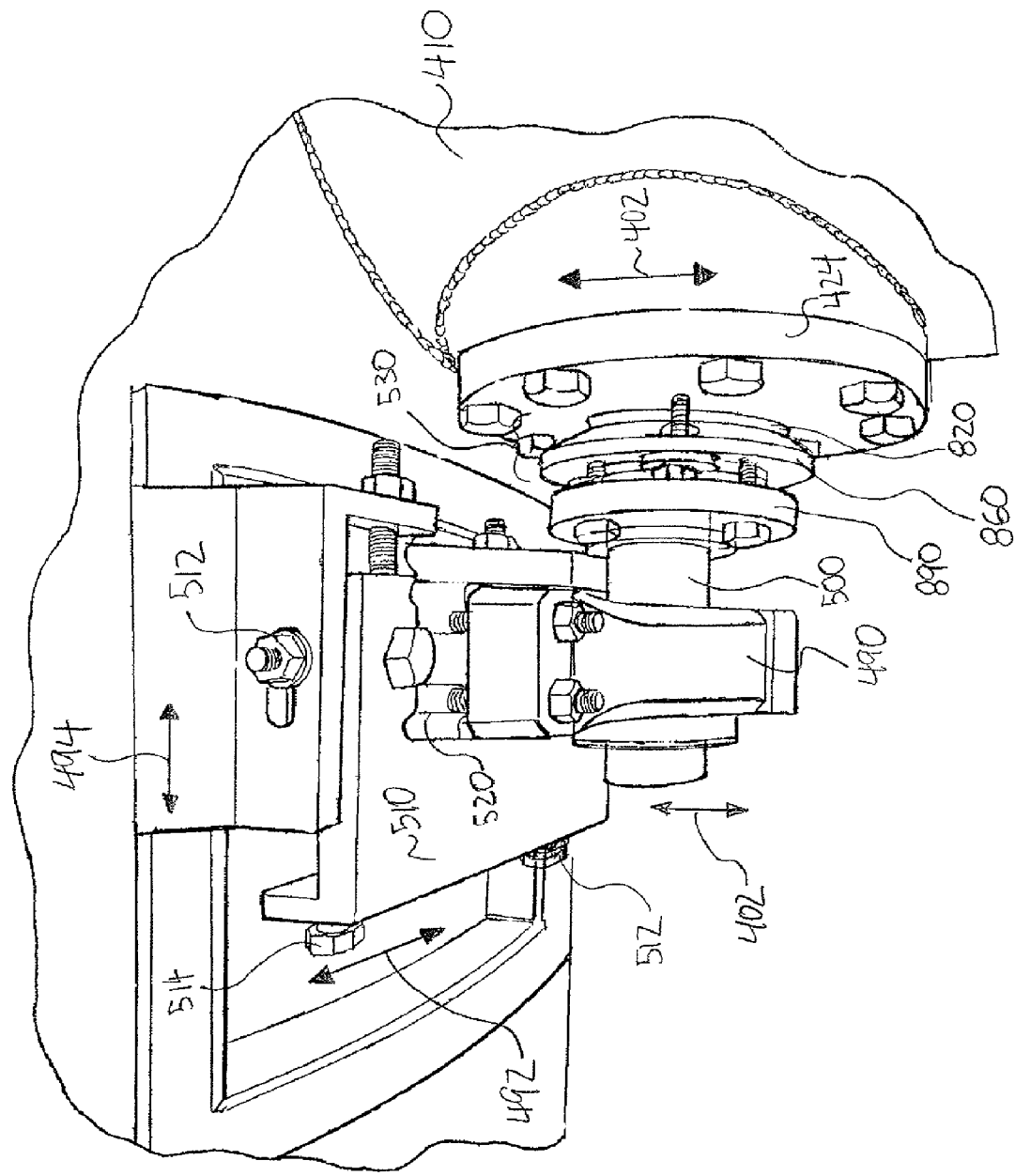
FIG. 4 is a perspective view of a bearing assembly along with the adjustment mechanism and adjustable seal.
Figure 5:
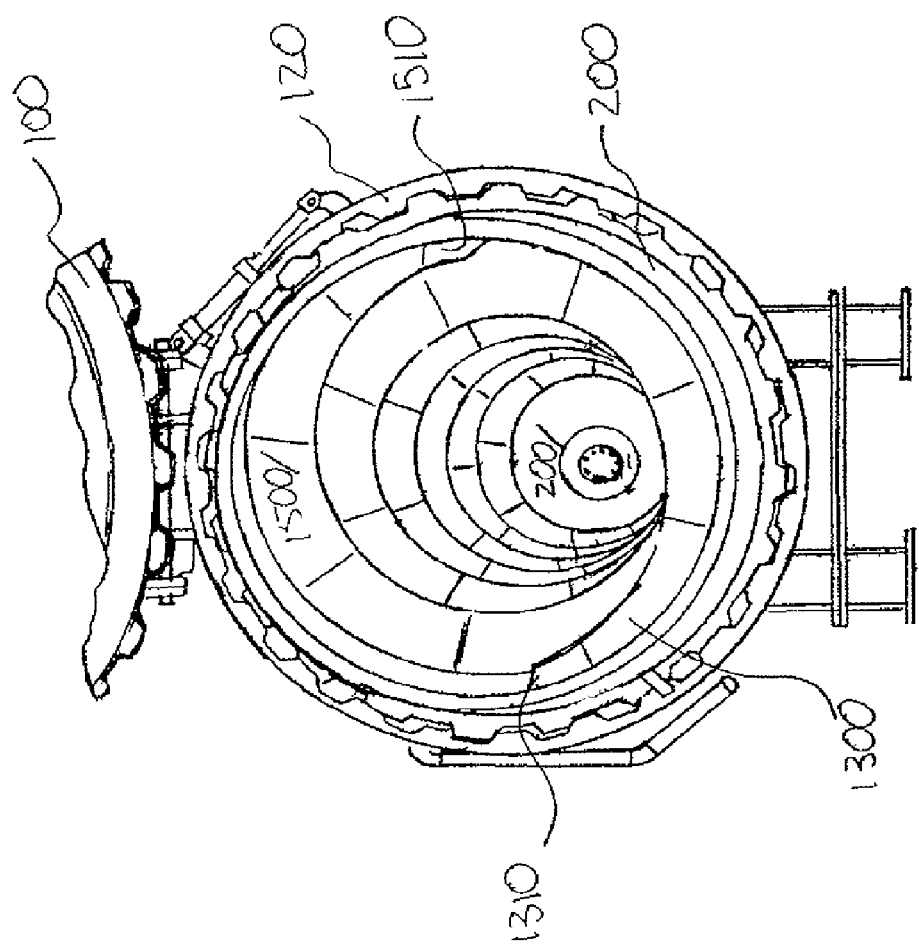
FIG. 5 is a front perspective view of one embodiment of a drum.
Figure 6:
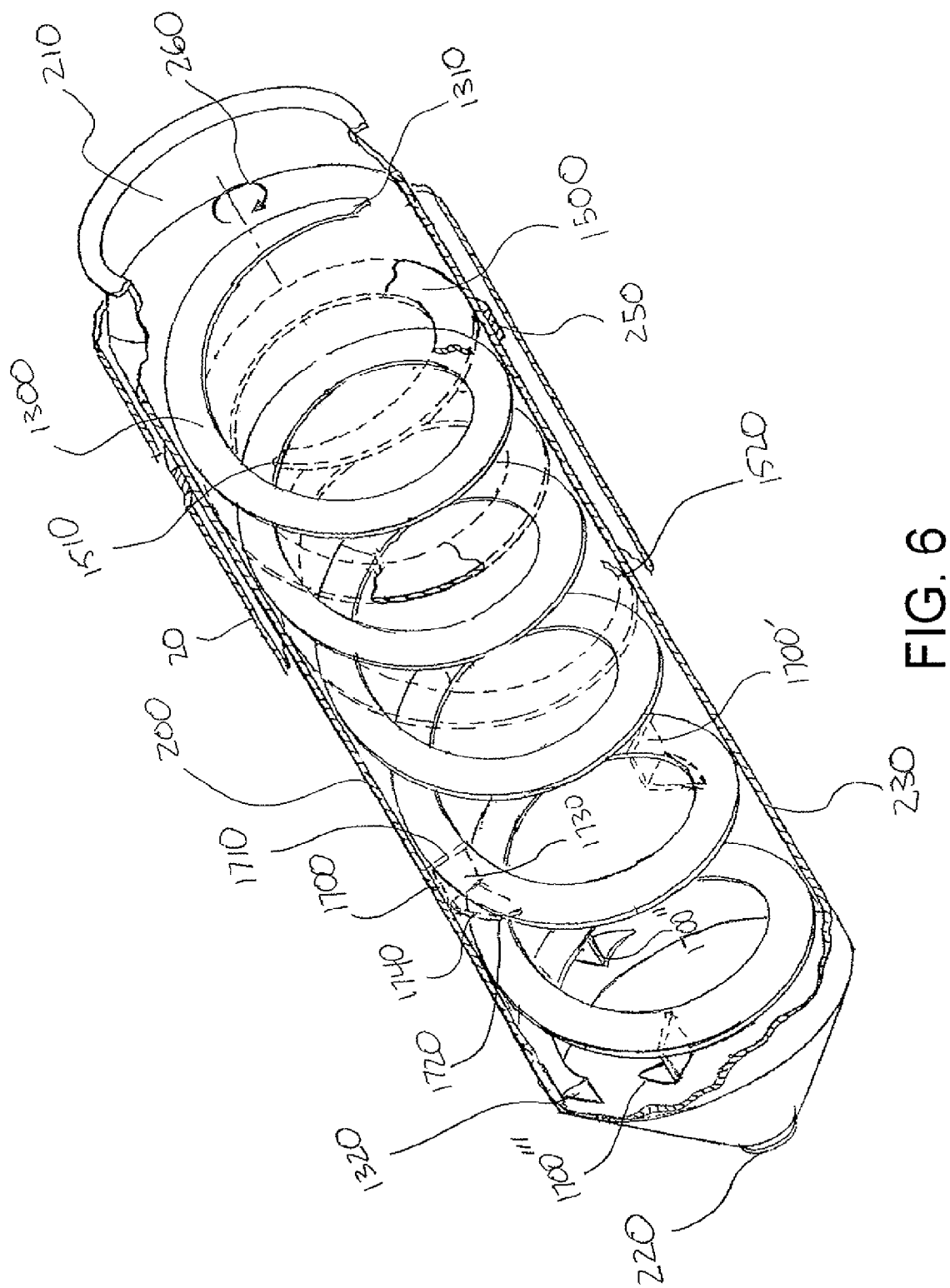
FIG. 6 is a cutaway perspective view showing a plurality of helixes and buckets or upsets.
Figure 7:
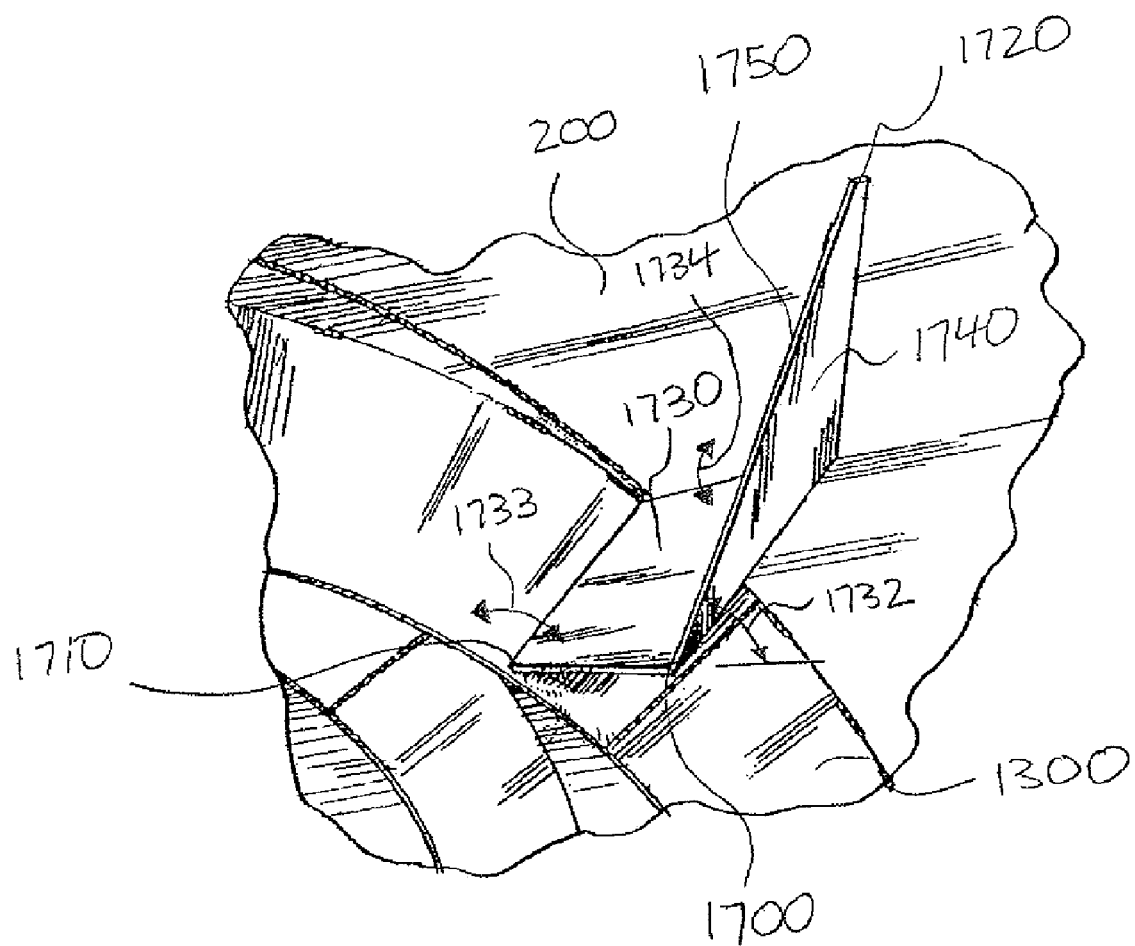
FIG. 7 is a perspective view of one embodiment for a bucket or upset.

FIG. 1 is a perspective view of the exterior of one embodiment of a processor 10 for treating materials. FIG. 2 is a perspective view of the exterior of one embodiment of a pressure vessel 10 with the end cap 100 opened. FIG. 3 is a perspective view of roller housing 410 with plate 416 opened exposing roller 400. FIG. 4 is a perspective view of bearing assembly 490, adjustable seal 530, and adjustment plate 510. FIG. 5 is a front perspective view of one embodiment of drum 200 with helixes 1300, 1500. FIG. 6 is a cutaway perspective view of drum 200 showing helixes 1300, 1500. FIG. 7 is a perspective view of one embodiment for a bucket or upset 1700.

Processor 10 can comprise vessel 20 and drum 200. In one embodiment drum 200 can be rotatively connected to vessel 20. In one embodiment a heavy walled processing pressure vessel 20 is used which can be generally cylindrical in configuration heavy walls can be used in the construction of vessel 20 to allow it to operate under conditions of high internal pressure as well as under vacuum conditions. Pressure vessel 20 can be mounted in a non-rotatable manner on a sturdy stationary support base 30 as shown in FIG. 1 (where support base comprises both sets of structural steel members 40), having a sufficiently wide expanse as to give ample stability. Support base 30 can use structural steel members 40 designed to effectively transfer the weight of processor 10 and its contained materials to the foundation under processor 10.

Drum 200 can be rotatively mounted inside of vessel 10 via shaft 310 (see FIG. 12) and support rollers 400 and 600. Drum 200 can transfer its forces to shaft 310 and support rollers 400, 600, which in turn transfer that load into the shell of vessel 20 and become a part of the load supported by support base 30, and finally transferred to the foundation below processor 10.

An end cap 100 (which may be dome shaped or substantially flat) can be provided with a sealing system such as locking ring 120. End cap 100 can be pivotally mounted close to inlet 50 of vessel 20. End cap 100 when closed can allow substantial pressure or a vacuum can be established inside vessel 20 at selected times.

Drum 200 can be located inside vessel 20. Drum 200 can be generally cylindrical in shape and mounted so as to be rotatable in either direction on its axis, which axis can be coincident with an axis of vessel 20. Drum 200 can be provided with a roller or support ring 250 adjacent its inlet end 210, with rollers 400,600 positioned to contact ring 250 and support inlet end 210 of drum 200. Inlet end 210 of drum 200 can be open and rear or second end 220 of drum 200 can be closed and fluid tight.

Figure 12:
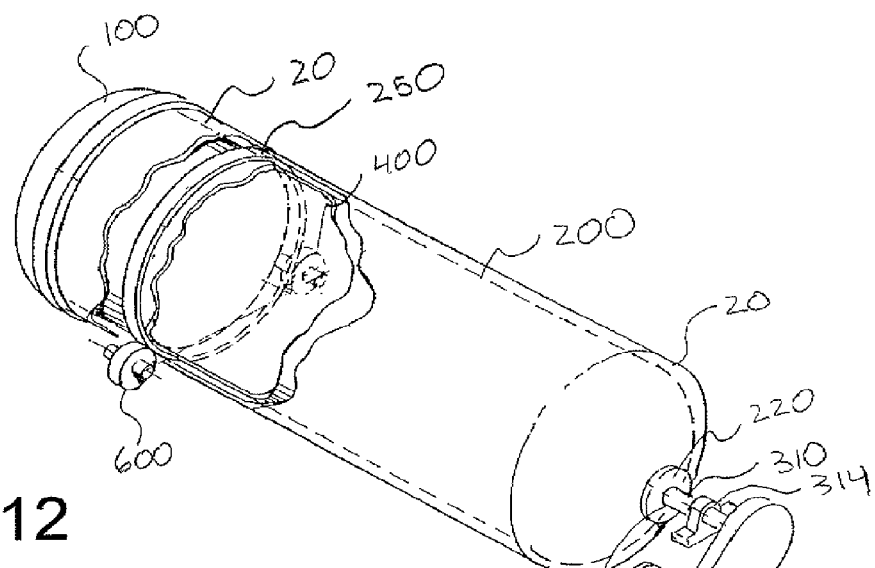
FIG. 12 is a perspective view showing a drum being supported by two rollers and a rear axle.

Connected to rear or second end 220 of drum 200 can be drive shaft 310, which can rotatively support rear or second end 220 of drum 200 and drive it in rotation. Drive shaft 310 can be rotatably supported by roller or ball bearings 314 (FIG. 12). This support arrangement can be configured to fix the location of drum 200 insofar as its horizontal positioning within vessel 20 is concerned.

Drive shaft 310 of drum 200 can penetrate the shell of vessel 20 and can be sealed from the atmosphere, such as by sealing means 318. One possible sealing means 318 can be of the type manufactured by Cherterton to enable a selected pressure or a selected vacuum to be maintained from time to time within vessel 20, and ultimately within drum 200.

In one embodiment the typical rate of rotation for drum 200 is between ½ and 30 revolutions per minute; between 2 and 30 revolutions per minute, between 5 and 25 revolutions per minute, between 5 and 15 revolutions per minute, and between 5 and 10 revolutions per minute, and preferably such rotational speed facilitates uniform loading of forces on drive assembly 300 which rotatively drives drum 200. In one embodiment variable (such as a high/low) speed control is used for drum 200 which can change drum speed from a low speed, such as ½ to a high speed, such as 10 revolutions per minute In one embodiment a VFD can be used for driving drum 200 which is infinitely variable.

In one embodiment drum 200 is capable of being rotated in either direction on its horizontal axis by means of drive assembly 300. In one embodiment drive assembly 300 can comprise reversible electric motor 320 and suitable reduction gearing 330 connected to drive shaft 310 of drum 200 to turn drum 200 in the selected direction. In one embodiment (not shown in the drawings) a heavy duty chain 340 passing over sprockets 350 and 360 for transferring the rotation of motor 320 to drive shaft 310 can be used in an arrangement familiar to those knowledgeable in the art. In one embodiment a hydraulic drive low speed medium torque (LSMT) or low speed high torque (LSHT) can be used.

General Description of Rotoclave Operation for one embodiment is provided below. Heat treatment of materials to be treated involves several steps that are typical of this type of processing. The following list includes various steps that are generally used. Combinations and omissions of some of the steps are allowed based on the types and/or the desired outcome of the treatment process.

(1) Load vessel (add processing water during this step (optional)).

(2) Close door and seal vessel.

(3) Pre-vacuum (optional step, also adding processing water during this step is optional).

(4) Heat-up (bring vessel and treatment materials up to processing temperature).

(5) Hold temperature (often called Time-at-Temperature ("TAT"), temperature is maintained for a pre-determined length of time determined by the process requirements).

(6) Cooldown and Drying (moisture is removed through evaporation (drying) thus causing the materials to cool).

(7) Vent vessel (without venting the vessel door could not be opened).

(8) Open vessel door.

(9) Discharge vessel drum contents (unload processed materials).

One embodiment for a Rotoclave Treatment Process follows. Prior to loading materials for processing end cap 100, is opened via opening mechanism 130. Materials can be loaded through the vessel opening of the first end 22. Methods of loading materials to be processed include conveyors that extend into the opening, a chute or hopper system utilizing carts, buckets, or tubs that dump materials into the chute/hopper and/or by hand. Materials need only be dropped in the vicinity of the drum inlet 210. Rotation of drum 200 in the first rotative direction will cause the materials to be conveyed towards the second end 220 of drum 200.

Once the materials are loaded, end cap 100 is closed forming an air-tight seal. The operator may now make a selection of process time and/or temperature and start the processing cycle. Normally, once the cycle is started the Computer Controller (PLC located in the control panel, 2000) takes over full control of all of the functions associated with the processing cycle. Normally, the next steps of treatment process are Pre-Vacuum and Water Injection. However, either, or both of these steps may be entirely omitted, being based on the requirements of the materials being processed.

This embodiment shows a process water control valve 2045 that is supplied with pressurized water used to inject process water through the steam line into the drum inlet. Vacuum may by produced using a vacuum pump, or with a steam-powered ejector. In FIG. 1 the vacuum device (in this instance a steam-powered ejector) 2031, is shown with a vacuum device control valve 2037, for activation. The suction port is of the vacuum device is connected to the vacuum system condenser 2032, creating negative pressure inside the condenser during operation of the device. The device being operated for a pre-programmed duration or until the desired negative pressure level has been reached. The discharge of the vacuum device passes into the after-condenser 2034, where the steam is condensed and non-condensables are vented to atmosphere via the non-condensables vent pipe 2030.

Heating of the materials to be processed begins as steam is introduced into the interior of vessel 20. The steam passes through a steam pressure control valve 2020, used to throttle steam flow to attain a desired down-stream pressure level. The steam control valve 2010 ensures that complete shut-off of the steam is attained as directed by the PLC.

As the temperature and pressure reach the desired levels the pressure control 2020, regulates the steam flow to maintain the desired pressure inside the vessel 20, throughout the programmed timed interval, often referred as, Time-at-Temperature ("TAT"). When the TAT time interval has been attained the steam control valve 2010, closes.

The contents of vessel 20 are now wet with condensed steam, including the interior of vessel 20, also the interior and exterior of drum 200. After the steam valve has closed vessel 20 and its contents are cooled and dried. The cooling/drying step begins when the main vapor valve 2035, opens. This allows stored heat inside the processed materials and vessel interior to be transferred to the vacuum system condenser 2032. Cooling water is pumped through the cooling water control valve 2040, and flows through the condenser tubes throughout the cooling and drying cycle.

The contents are cooled and dried as long as free moisture is present. Once the metal surfaces are dry then no more cooling due to evaporation occurs. The processed materials continue to cool as long as free moisture is present and as long as the materials have not cooled below the vapor pressure. The vacuum device 2031, creates a vacuum on the shell of the vacuum system condenser 2032, this causes a vacuum inside vessel 20 (pressures below atmospheric pressure) and promotes cooling the processed material to 150° F. (66° C.) and lower.

Once vessel 20 has cooled sufficiently then main vessel vent valve 2024, opens. This allows air to enter vessel 20 so the pressure inside vessel 20 is equalized with atmospheric pressure. Opening this valve also unlocks the lock ring interlock so the first end 22, may be opened.

Condensate from vessel 20 collects in the annular space between the interior of vessel 20 and the exterior of drum 200. This condensate is normally drained from the system at the end of the cycle. At the same time, the vacuum system condenser 2032, delivers condensate to the condensate water collection tank 2060, via a pipe connection. Each of these collection volumes operate at vessel pressure during cooldown and drying, and can only be drained only when the vessel has been vented to atmospheric pressure or, in some cases, when the vessel is still under pressure. Condensate water is sent to drain 2050, flow being controlled by drain valve 2051. As with most steam heated vessels a pressure relief valve 2022 can be provided for safety.

FIG. 6 is a schematic diagram of one embodiment of drum 200. FIG. 5 is a front perspective view of one embodiment of a drum 200. FIG. 7 is a perspective view of bucket or upset 1700 attached to a portion of helix 1500.

One purpose of internal helix flighting is to move materials being processed either towards the rear of drum 200 (inward) or in the opposite direction, towards drum 200 inlet, as drum 200 rotates about its central axis. The direction of rotation causing an inward movement of the contents being treated can be called the loading direction. This is because it is the rotational direction that drum 200 turns when drum 200 is being loaded. During processing or treatment drum 200 normally operates in the loading direction thus continually moving the contents being treated or processed towards the rear of drum 200.

In one embodiment the interior of drum 200 can be equipped with a series of helical flighting 1300,1500 to facilitate agitation and movement of materials as a consequence of rotation of drum 200. In one embodiment helical flighting 1300,1500 can be offset at an angle from the sidewall of drum 200, such that a radial line from the longitudinal center of drum and intersecting with a helical flighting would make an angle, such as 14 degrees. In one embodiment a plurality of upsets or lifting buckets 1700 can be attached to the helical flighting 1300 and/or 1500. In one embodiment helical flighting 1300 can begin with first end 1310 and end with second end 1320. In one embodiment helical flighting 1500 can begin with first end 1510 and end with second end 1520. In one embodiment helical flighting 1500 takes up about one half of the longitudinal length of drum 200 while helical flighting 1300 takes up about all of the longitudinal length of drum 200. In one embodiment the percentages of longitudinal length taken up by helical flighting 1500 vary between the following percentages from front to rear and from rear to front (along with any range between any one of the possible specified percentages): about 5, 10, 15, 20, 25, 30, 35, 40, 45, 50, 55, 60, 65, 70, 75, 80, 85, 90, 95, 97, 99, 100. In one embodiment helical flighting 1300 can also vary between the same percentages and positions which may be different from the spanning of helical flighting 1500.

Certain process materials may tend to pack against the rear face of drum 200 if only helical flighting are used inside drum 200. To avoid this problem upsets or buckets 1700 can be used which can be affixed to or separated but adjacent to the rear of the helical lighting (attached to the side of the helix that faces the rear of drum 200). The helical flighting can be constantly moving process materials towards the rear of the drum, and one or more upsets or buckets 3700 can move a portion of the materials being treated or processed back upstream, towards the inlet of drum 200. The combination of helical flighting and upsets or buckets 1700 can cause a beneficial circulation of the materials being treated or processed and substantially eliminate compaction and stratification of the materials being treated or processed. An additional benefit of using upsets or buckets 1700 is that they tend to not substantially affect the materials treated or processed as they are being discharged from drum 200. This is because upsets or buckets 1700 occupy the space adjacent to the rear of the helical flighting. During discharge from drum 200 of the materials processed or treated, the front side of the helical flighting tends to move the materials. Therefore, upsets or buckets 1700 located on the opposite (rear) side of the helical flighting tend to not impact materials during discharge.

In one embodiment vessel 20 can be operated on an incline 70 (see FIG. 1). In one embodiment a 7 degree angle of incline 70 from the horizontal, with the front or inlet end 22 being higher than the closed lower second end 60 of vessel 20. The angle of incline 70 aids in moving materials to be processed within drum 200 in that such materials will be moved through drum 200 toward its second or back end 220, at least partly under the influence of gravity as drum 200 is rotated.

The size of drum 200 is not of particular importance. It is noted that a drum 200 approximately ten feet long is of a size that can be effectively utilized in a hospital or a large medical office, for example, where it is extremely convenient to be able to get rid of contaminated medical waste on the premises, making unnecessary the shipment of the contaminated waste to another location for disposal. Smaller sized versions of processor 10 could take the form of a unit that could be placed within a relatively limited area, to handle medical type waste materials generated therein. Larger units can perform large scale operations. However, the diameter of drum 200 should be sufficiently large to accept materials upon which a prior size reduction has not taken place. Any combination of reasonable diameters and lengths can be used, limited only by practicality. One limit on size can be shipping restrictions for trucks over roads and highways. This limit is 12 feet in diameter and 50 feet long (366 centimeters in diameter and 1,252 centimeters long), and even this size requires special permits for oversize shipments. Above this size, shipment by standard means generally becomes impractical. On the other hand, the fabrication of units of virtually unlimited size can be constructed on the site of a proposed operation, accomplished by utilizing special fabrication techniques.

Lifting buckets or upsets 1700 can be mounted on the interior of drum 200. In one embodiments buckets 1700 are arranged so as to minimize any obstruction of flow of materials within drum 200 during removal of material. Lifting buckets 1700 can be connected to one of the helixes 1500 (see FIGS. 6 and 7). In one embodiment lifting buckets 1700 can be connected to both helixes 1300,1500. In one embodiment lifting buckets 1700 can be attached to only a portion of one of the helixes 1500. In one embodiment lifting buckets 1700 can be attached to only the rear most portion of drum 200, such as the last one third of drum 200. In one embodiment, lifting buckets 1700 can by radially spaced about one of the helixes 1500. In one embodiment, between 3 to 4 lifting buckets 1700 can be attached to one of the helixes. In one embodiment lifting buckets 1700 can be attached to at least one of the helixes 1300,1500 on the rear most sides, the sides facing rear or second end 220 of drum 200 (placing on such side of a helix will tend to minimize the impact of any lifting bucket 1700 during the process of unloading drum 200). In one embodiment lifting buckets 1700 can be radially spaced about one or both helixes 1300,1500, such as about 120 degrees apart. In one embodiment only one helix (e.g., 1500) may have buckets 1700, or even have buckets 1700 spaced about the rear one half of its longitudinal axis. As shown in FIG. 6 lifting buckets 1700, 1700', 1700", and 1700''' can be used in a spaced apart orientation along helix 1500. In FIG. 6 lifting bucket 1700 is shown for clarity in a "reversed position" and should be constructed such that it faces the preferred direction of rotation when drum 200 is rotated to cause items to move towards rear 220 (such as shown with buckets 1700', 1700", and 1700''').

Lifting buckets 1700 can comprise base 1710, tip 1720, first section 1730, transition 1735, second section 1740, and decreasing portion 1750. First and second sections 1730,1740 can be at angle 1734 relative to the wall of drum 200 (which can be 90 degrees or other angles). First section 1730 can be at angle 1733 relative to helix 1500 (such angle 1733 can be 90 degrees or 104 degrees) to which it is connected. Second section 1740 can be at an angle 1732 relative to first section 1730. Such angle 1732 can be between about 1 and 89 degrees, between about 15 to 85 degrees, between about 20 to 70 degrees, between about 25 to 65 degrees, between about 30 to 60 degrees, between about 30 to 55 degrees, about 30 degrees, about 45 degrees, or about 60 degrees. Decreasing portion 1750 can be curved or a straight line.

In one embodiment upsets or buckets 1700 can include only first section 1730. In one embodiment first section 1730 can be a rod. In one embodiment first section 1730 can extend below the top of helical flighting 1500. In one embodiment a space can exist between first section 1730 and drum 200. In one embodiment this space can be shaped, such as semicircular, rectangular, trapezoidal, triangular, etc. In one embodiment only a portion of first section 1730 contacts drum 200. In one embodiment a space can exist between first section 1730 and helical flighting 1500. In one embodiment this space can be shaped, such as semicircular, rectangular, trapezoidal, triangular, etc. In one embodiment only a portion of first section 1730 contacts helical flighting.

In one embodiment second section 1740 can extend below the top of first section 1730. In one embodiment a space can exist between second section 1740 and first section 1730. In one embodiment this space can be shaped, such as semicircular, rectangular, trapezoidal, triangular, etc. In one embodiment only a portion of second section 1740 contacts drum 200. In one embodiment a space can exist between second section 1740 and drum 200. In one embodiment this space can be shaped, such as semicircular, rectangular, trapezoidal, triangular, etc.

The helical flighting 1300,1500 can be attached to the interior perimeter of drum 200 so as to minimize obstruction of flow of materials within drum 200. The angularity of helical flighting 1300,1500 can be such that when drum 200 is rotated in a first rotative direction, the materials to be processed are moved forward, toward the closed lower or second end 220 of drum 200, whereas rotation of drum 200 in the second rotative direction causes the materials to be moved backward toward inlet opening 210 of drum 200. Helical flights which can be continuous or segmented. If they are segmented then the segments can be offset with overlapping ends such that the overlapping flights could pump fluid when the drum is rotated in the same why that the continuous flights pump fluid. Helical flighting 1300, 1500 can be continuous throughout the length of drum 200. In one embodiment helical flighting 1500 is continuous throughout the length of drum 200, while helical flighting 1300 begins adjacent inlet 210 of drum 200 but stops short of rear or second end 220 of drum 200. In one embodiment, helical flighting 1300 continues through about two-thirds of the length of drum 200. As is obvious to those skilled in the art, the size and frequency of upsets or lifting buckets 1700, the angle of incline of drum 200, and the rate of rotation of drum 200 are variable and are a function of the required rate of movement of materials within drum 200 and the amount of material to be processed in a given amount of time.

Individual buckets 1800 and targets (e.g., sets of plurality of projections 1870) can be designed to work together to provide improved impact and tearing of materials being processed or treated. During rotation of drum 200 buckets 1800 scoop up a portion of the materials which lifts this portion above the main body of materials being processed or treated. One embodiment places bucket 1800 so that materials fall in the direction of a target, such as plurality of projections 1870. The target can be designed with a series of points or projections that improve damage probability of items hitting the target, thereby tending to open such items for improved treatment or processing. Buckets 1800 can also act as targets themselves and also employ a series of projections that improve damage probability.

Figure 8:
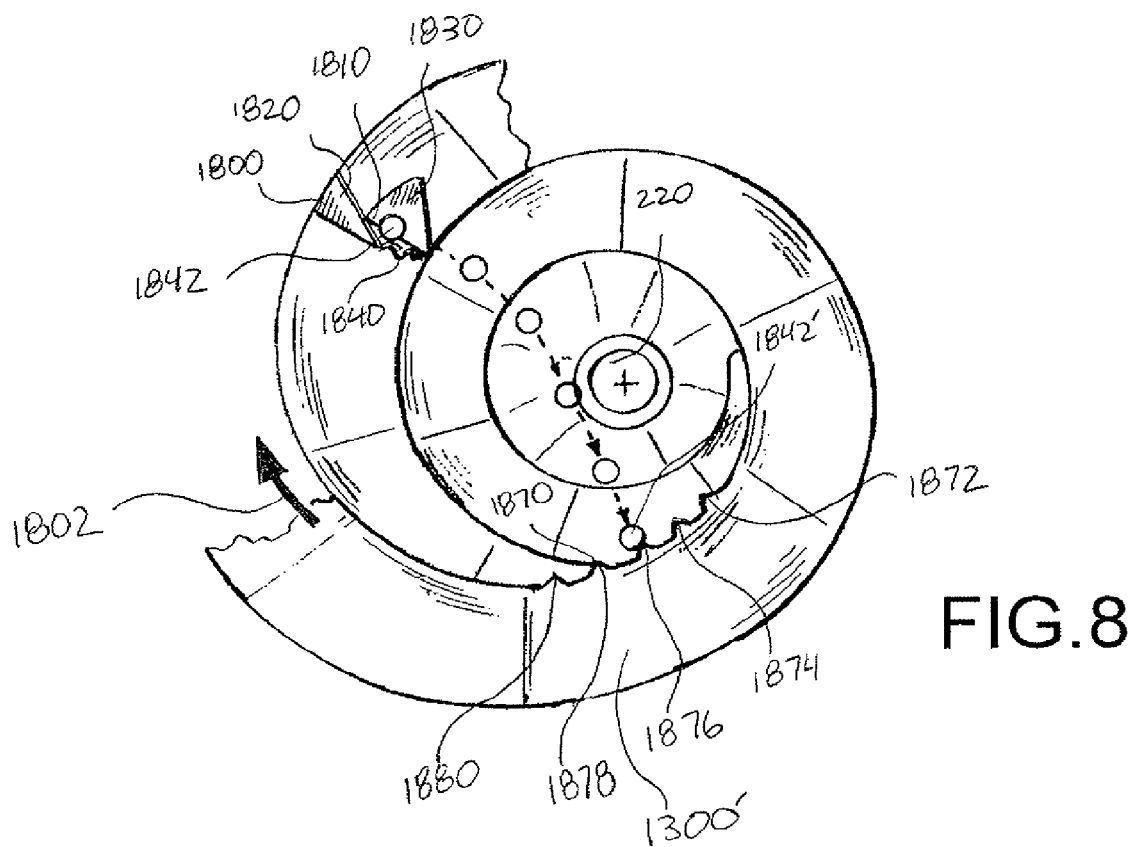
FIG. 8 is a front view of an alternative drum.

FIG. 8 shows an alternative embodiment for a lifting bucket 1800. Lifting bucket 1800 can comprise base 1810, first side 1820, and second side 1830. Lifting bucket 1800 can include plurality of projections 1840 which can be located on base 1810. Alternatively plurality of projections can be located on base 1810, first side 1820, and/or second side 1830. Plurality of projections can cut/slice items located in drum 200 during rotation. FIG. 8 also shows an alternative helix 1300' which includes plurality of projections 1870. Plurality of projections 1870 can comprise projections 1872,1874,1876,1878, and 1880. Plurality of projections 1870 can be located so that items picked up by a bucket 1800 tend to fall on plurality of projections 1870 to allow plurality of projections to cut/slice/open such items. Shown in FIG. 8 item 1842 got through a path falling on projection 1876 (as indicated by the position of item 1842). Sets of plurality of projections 1870', 1870", 1870'", etc. can be located a various points of helix 1300'. Additionally, buckets 1800', 1800", 1800'", etc. can be included to match up with plurality of projections 1870', 1870", 1870'", etc. Additionally, helix 1300 can include one or more buckets 1800 and plurality of projections 1870.

One processing or treatment challenge associated with constant rotation of drum 200 is that fabrics and plastic strapping/film can "ball up" together or create large "snake like" masses of connected fabric and fabric-like materials. For the materials being processed or treated, these "balls" or "snake like" masses create handling problems for the down stream equipment and is to be avoided. In one embodiment hook-shaped protuberances (e.g., made of stainless steel) can be used to substantially reduce these "balls" or "snake like" formations. The hook-shaped protuberances can be either connected to the top of the helical flighting or to the inner surface of drum 200. These protuberances can pass through balls or snakes in materials being processed or treated, as they are forming, and grab one or two items, pulling them away from the formation. This action can continue throughout processing or treating and thus prevent or retard development of masses of interconnected fabrics or materials.

Figure 9:
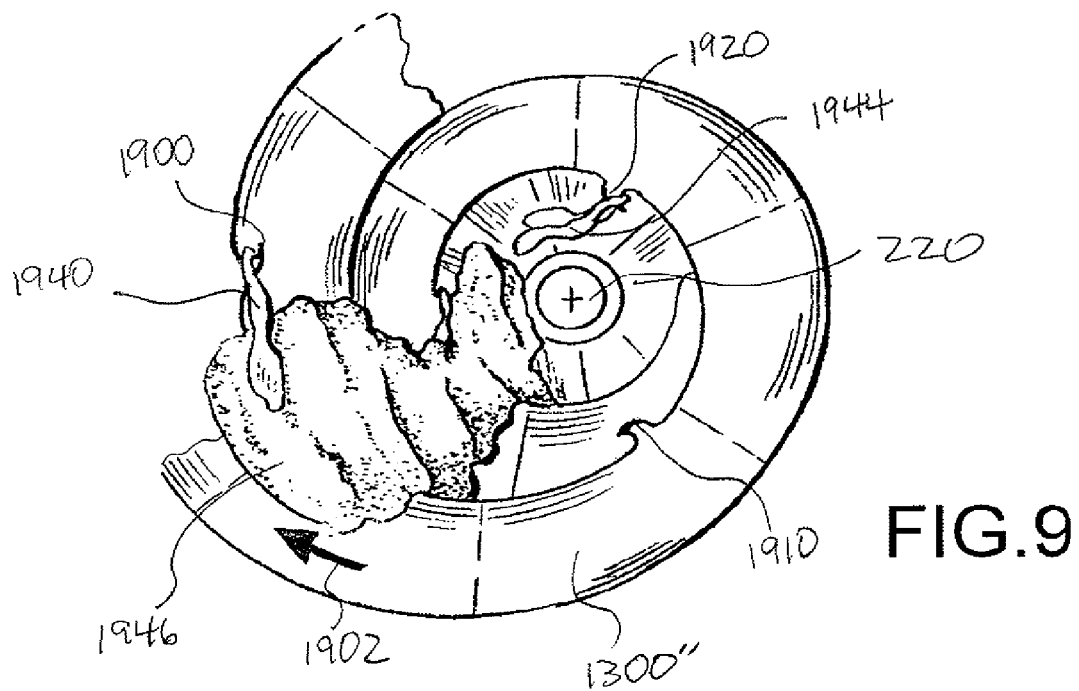
FIG. 9 is a front view of another alternative drum.
Figure 10A:
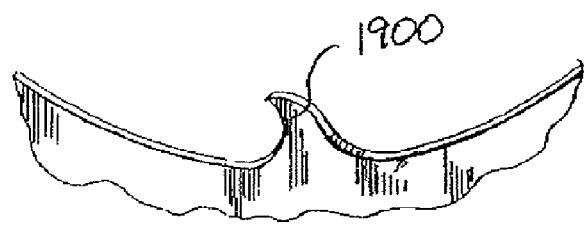
FIGS. 10A, 10B, 10C, 10D, and 10E show various embodiments for hooks or upsets.
Figure 10B:
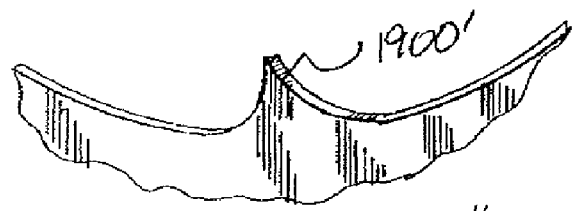
Figure 10C:
Figure 10D:
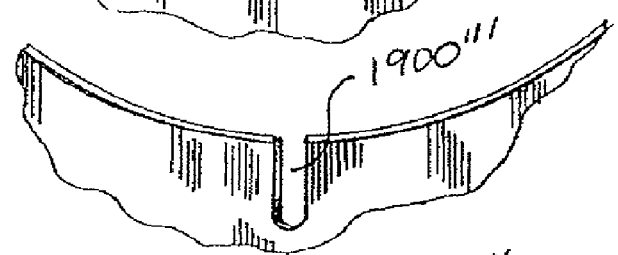
Figure 10E:

FIG. 9 shows an alternative helix 1300" which includes a plurality of hooks 1900, 1910, 1920, and 1930. Such hooks can be used to tear/rip/cut/slice items located in drum 200 during rotation (e.g., items 1942 and 1944), such as in the direction of arrow 1902. In FIG. 9 each hook is show pointed in the direction of arrow 1902 so that tearing/ripping/cutting/slicing action will occur during rotation in the direction of arrow 1902, but not during rotation in the direction opposite of arrow 1902. With such configuration the action of the hooks can occur such as during treatment when material to be treated 1946 is being pushed to the rear 220 of drum 200 (e.g., when drum 200 is being rotated in the direction of arrow 1902), but not during the emptying stage of drum 200 (e.g., when drum is being rotated in the opposite direction of arrow 1902). Alternatively, hooks pointing in both directions (arrow 1902 and opposite of arrow 1902) can be used. Also alternatively, hooks tending to point to the longitudinal center of drum 200 can be used. Also alternatively, a plurality of hooks pointing in the direction of arrow 1902 along with a plurality of hooks pointing in the opposite direction of arrow 1902 can be use.

FIGS. 10A through 10E show various alternative embodiments for hooks 1900, 1900', 1900", 1900'", and 1900"". These can be various shapes for "clothing hooks." FIG. 10C can be a rod. Such hooks can be mounted on the edge of a helix 1300,1500 and/or on the inner surface of drum 200.

In one embodiment the diameter of drum 200 needs to be of a sufficient volumetric capacity to accept a selected quantity of material to be processed, with an additional space of approximately 30% of the volume of the interior diameter of drum 200 remaining vacant to allow materials to fall and to mix within drum 200 as it rotates. In this embodiment, additional processing capacity can be added to processor 10 by increasing its length. The ratio of diameter to length is variable and depends upon the amount of material to be processed in a given amount of time in concert with the size and frequency of the agitation mechanisms of the drum to insure complete mixing of materials.

Figure 11:
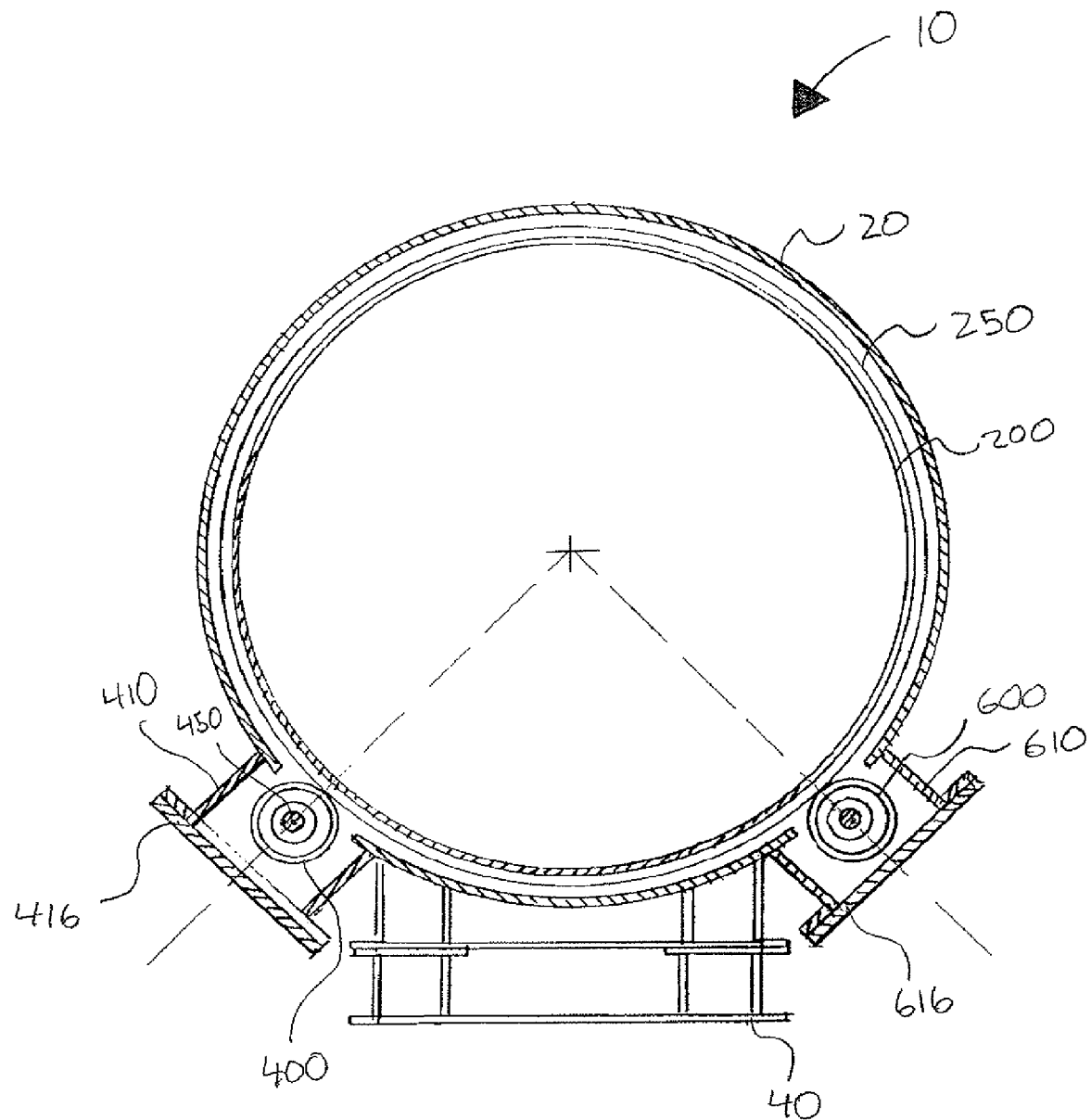
FIG. 11 is a schematic view of two rollers supporting the drum in the vessel.
Figure 13:
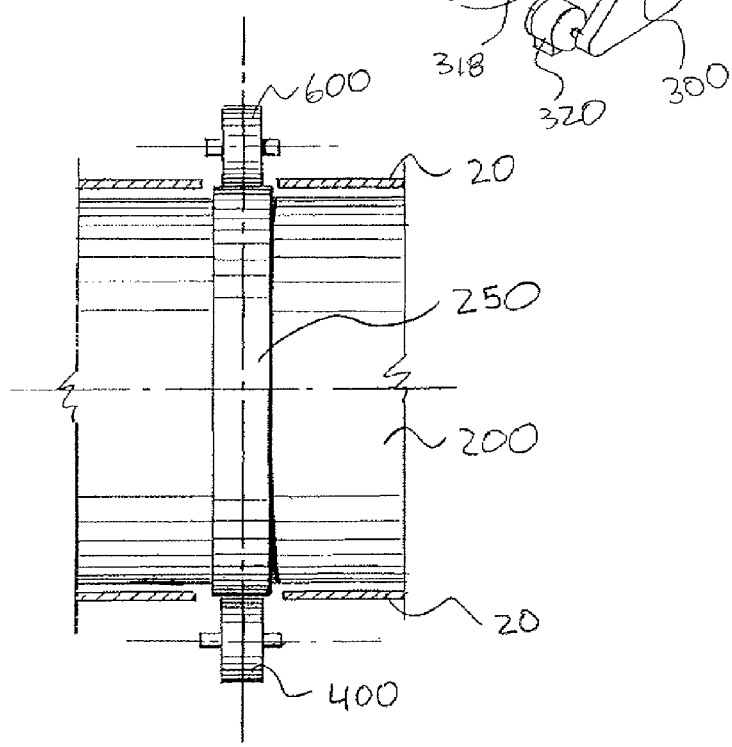
FIG. 13 is a bottom view showing two rollers support a drum.
Figure 14:
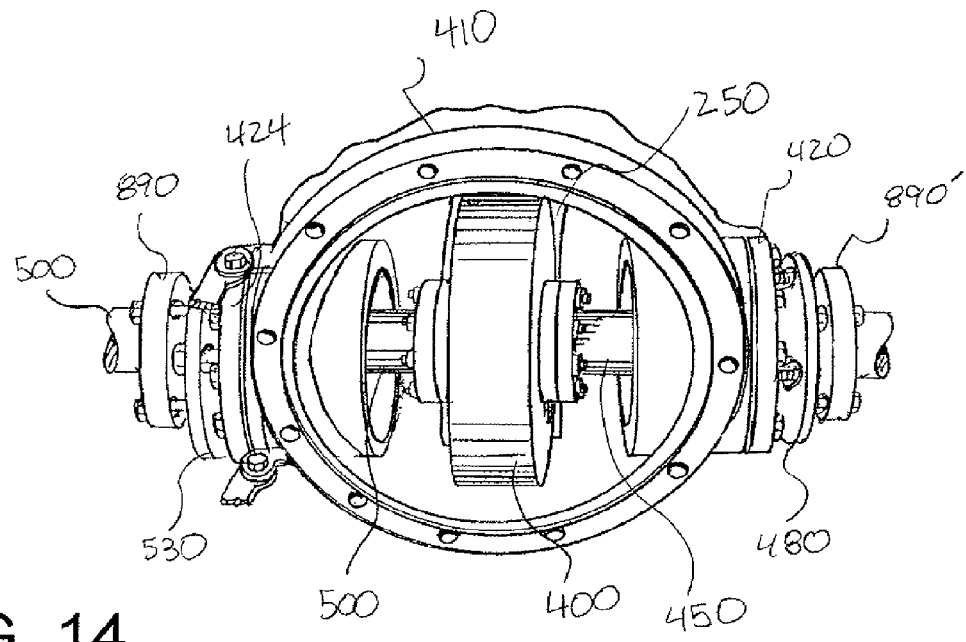
FIG. 14 is a perspective view of a roller housing opened and showing a roller supporting a drum.
Figure 15:
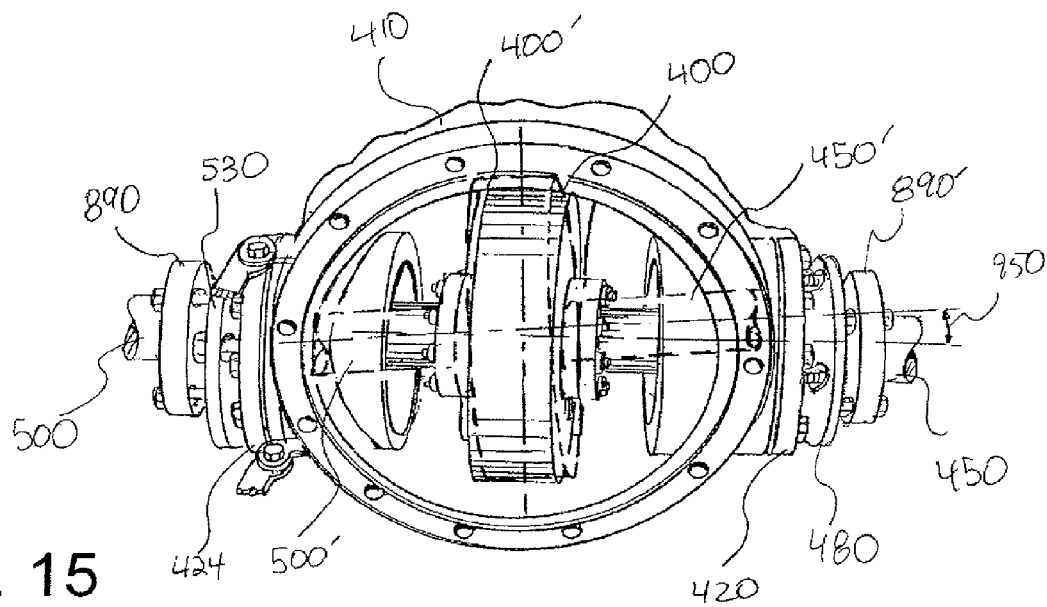
FIG. 15 is a perspective view of a roller housing opened and showing a roller supporting a drum, and also showing the roller being adjusted in relation to the position of the roller shown in FIG. 14.
Figure 16:
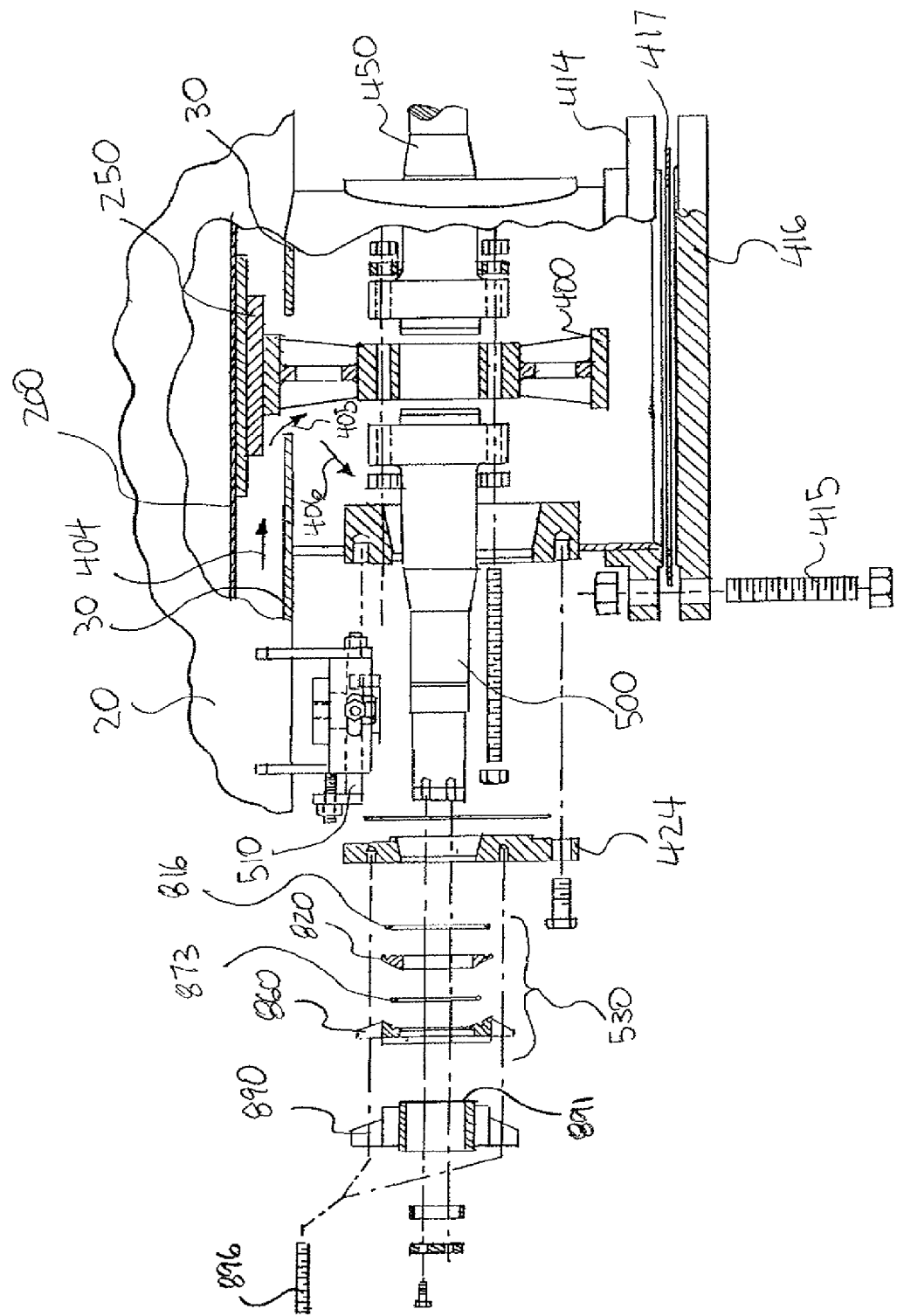
FIG. 16 is a partially exploded sectional view of a roller housing and roller.

FIG. 11 is a schematic view of two rollers 400,600 supporting drum 200 in vessel 20. FIG. 12 is a perspective view of two rollers 400,600 (along with axle 310) supporting drum 200. FIG. 13 is a bottom view of rollers 400,600 supporting drum 200 (where part of vessel 20 has been removed to more clearly see drum 200 and rollers 400,600). FIG. 14 is a perspective view of roller housing 410 opened and showing a roller 400 supporting drum 200. FIG. 15 is a perspective view of roller housing 410 opened and showing roller 400 supporting drum 200, and also showing roller 400 being adjusted in relation to the position of roller 400 shown in FIG. 14. FIG. 16 is a partially exploded sectional view of roller housing 410 and roller 400. Roller housing 610 can be constructed substantially similar with substantially similar components as those in roller housing 410. Accordingly, only roller housing 410 and its components will be described in detail.

As shown in FIGS. 11-13 drum 200 can be rotatively supported by two rollers 400,600. Rollers 400,600 can be contained respectively in housings 410,610. Because the construction of rollers and their bearing systems are substantially the same, only roller 400 will be explained in detail. Roller 400 can rotatively support drum 200, such as by contact with roller ring 250. Roller 400 can be rotatively supported by vessel 20 through roller housing 410. Because drum 200 is preferably exactly parallel to vessel 20, preferably there is a means to adjust roller 400 relative to drum 200. In one embodiment roller 400 can be adjustably mounted to allow full width of contact between roller (e.g. roller ring 250) 400 and roller ring 250. Such perpendicular interfacing can minimize wear between roller 400 and drum 200 (e.g., roller ring 250). Such perpendicular interfacing can also reduce vibration and frictional resistance during rotation of drum 200. Adjustment of roller 400 can be assisted by using a marking liquid on roller 400 and viewing the pattern made on drum 200 during rotation. In one embodiment support rollers 400, 600 can be positioned non-symmetrically so that as materials being treated climb the wall of rotating drum 200 due to its rotation, the loads on the two support rollers 400,600 are more nearly equalized. It is believed that approximately a 5 degree angular offset will more equalize the loads on support rollers 400,600. One or both of rollers 400,600 can be offset to accommodate non-symmetrical loading during rotation.

Roller 400 can be rotatively supported in housing 410 by shafts 450,500. Shafts 450,500 can themselves be rotatively supported by bearings 440,490. Bearings 440,490 can be adjustably mounted to vessel 20 through use of adjustable mounts 460, 470 and 510,520. It has been found that the life of bearings are substantially shortened when exposed to the operating environment of treatment system 10. Preferably, bearings 440,490 are located outside of vessel 20 to prevent exposure to harmful environments (e.g., heat, water, steam, high pressures and temperatures, and vacuum) during operation of processing system 10. Because the interior of roller housing 410 is exposed to the working environment of processing system 10, in one embodiment a sealing system can be provided between the interior of housing 410 and its exterior rotating shafts 450,500. However, because shafts 450,510 preferably are adjustable relative to drum 200 (to provide a perpendicular contact surface with support ring 250), such shafts should be adjustable relative to housing 410, but capable of maintaining a seal after adjustment is completed.

As shown in FIGS. 3 and 4 bearing 440 can be adjustable relative to vessel 20 in the directions of arrows 442,444 through adjustment plate 460 by the adjustment means 462, 464 which can be adjustment screws. Adjustability in the directions of arrows 444 can be achieved using adjustment plate 460 by adjustment means 462, which can be one or more adjustment screws. Adjustability in the direction of arrows 442 can be achieved using adjustment plate 460 by adjustment means 464, which can be one or more adjustment screws. Adjustability in the directions of arrows 401 can be achieved by shim 470.

As shown in FIGS. 3 and 4 bearing 490 can be adjustable relative to vessel 20 in the directions of arrows 492,494 through adjustment plate 510 by the adjustment means 512, 514 which can be adjustment screws. Adjustability in the directions of arrows 492 can be achieved using adjustment plate 510 by adjustment means 512, which can be one or more adjustment screws. Adjustability in the direction of arrows 494 can be achieved using adjustment plate 460 by adjustment means 514, which can be one or more adjustment screws. Adjustability in the directions of arrows 402 can be achieved by shim 520.

Preferably adjustable seals between shaft 450 and housing 510 along with shaft 500 and housing 510 can be provided. Because both adjustable seals can be of substantially the same construction, the construction of only one adjustable seal (e.g., 530 or 800) will be provided, which is shown in FIGS. 24 and 14-27.

Figure 17:
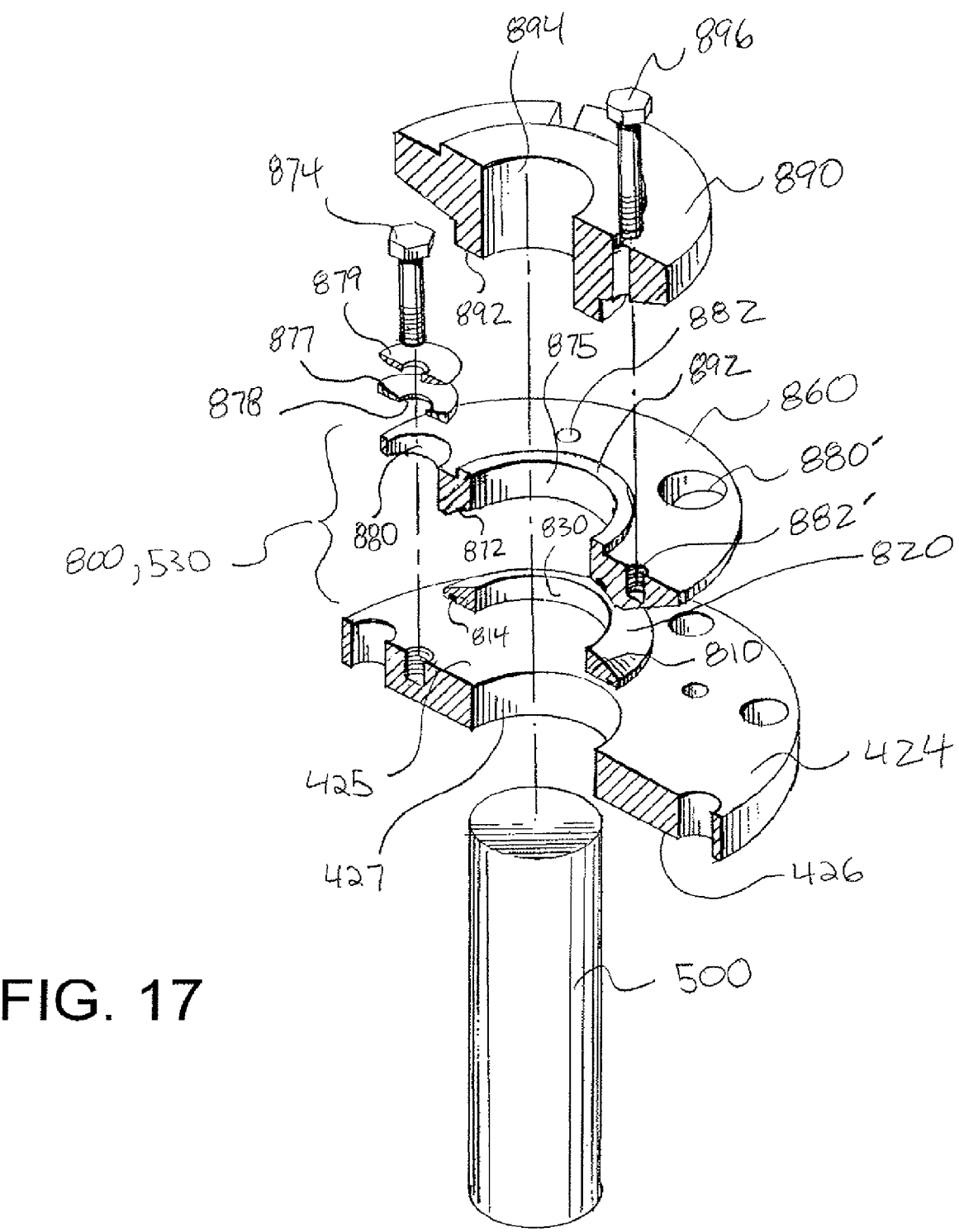
FIG. 17 is an exploded sectional view of various components of an adjustable sealing assembly.
Figures 18, 19, 20:
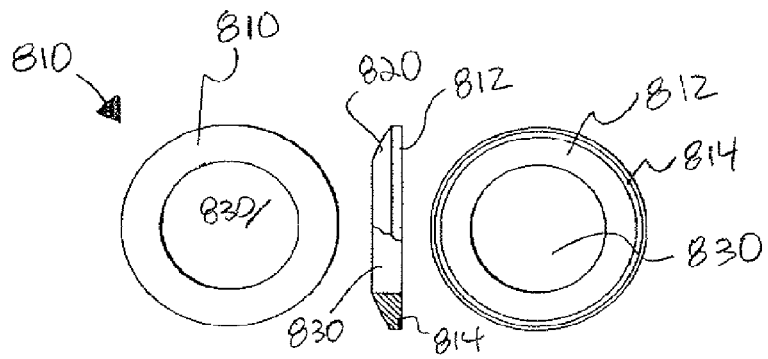
FIGS. 18, 19, and 20 are respectively top, side, and bottom views of the convex piece.
Figures 21, 22, 23:
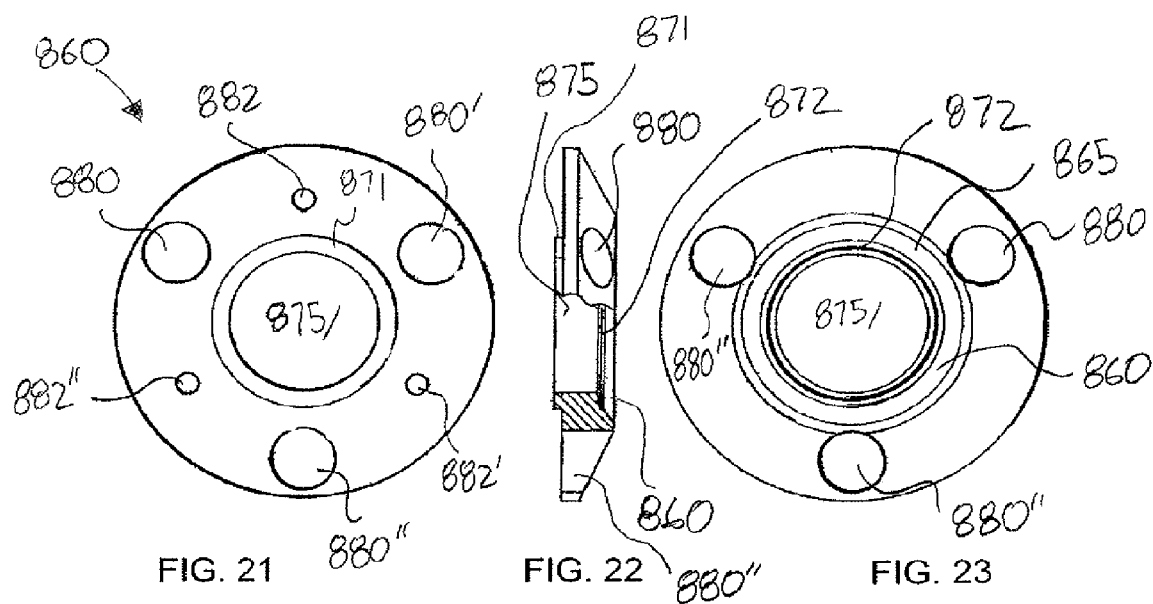
FIGS. 21, 22, and 23 are respectively top, side, and bottom views of the cup.

FIG. 16 shows a sectional view of one embodiment of an adjustable seal 800 with shaft 500 centered with respect to seal 530. FIG. 17 is an exploded of an adjustable seal 530, 800. FIGS. 18-20 are top, side, and bottom views of convex portion 820. FIGS. 21-23 are top, side, and bottom views of cup 860. Adjustable seal 530 can comprise convex portion 810 and cup 860. Convex portion 810 can movably fit within cup 860. Convex portion can comprise base 812, upper surface 820, and bore 832. Base 812 can include peripheral groove 814, which preferably can house a sealing component, such as an O-ring. Cup 860 can comprise base 865 and upper surface 870. Upper surface 820 of convex portion 810 can movable fit within base 865 of cup 860. Base 865 can be "bowl" shape to fit upper surface 820. Base 865 can include groove 872, which preferably can house a sealing unit, such as an O-ring. In this manner a seal can be maintained between convex portion 810 and cup 860 even where relative movement (e.g., rotational and/or spherical in three dimensions) between the two pieces is seen. Additionally, the sealing unit in convex portion 810 can maintain a seal between base 812 and a contacting surface even where sliding movement is seen between convex portion 810 and a contacting surface, such as plate 424. A conventional seal can be maintained between collar 890 and shaft 500. A conventional seal can be maintained between collar 890 and cup 860. A conventional seal can be maintained between plate 494 and roller housing 410. In such manner a seal between shaft 500 and roller housing 410 can be maintained in various orientations of shaft 500 to housing 410. Various movements will be reviewed below.

Figure 25:
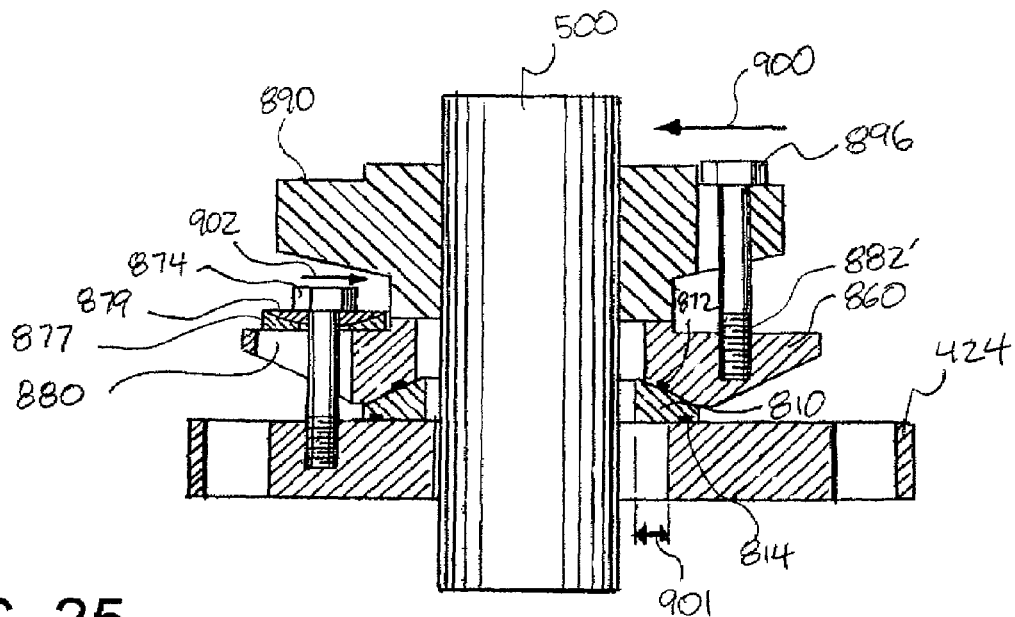
FIG. 25 shows a sectional view the adjustable seal of FIG. 24 with the shaft being offset with respect to a plate for a roller housing.

FIG. 25 shows a sectional view adjustable seal 530 with shaft 500 being offset in the direction of arrow 900 with respect to seal 530 a distance 901. Arrow 902 indicates that fastener 874 has slid over to absorb the movement indicated by arrow 900. Even so shifted a seal can be made between convex portion 810 and plate 424 through a sealing unit located in groove 814. Additionally, a seal can be made between convex portion 810 and cup 860 through a sealing unit located in groove 872.

Figure 26:
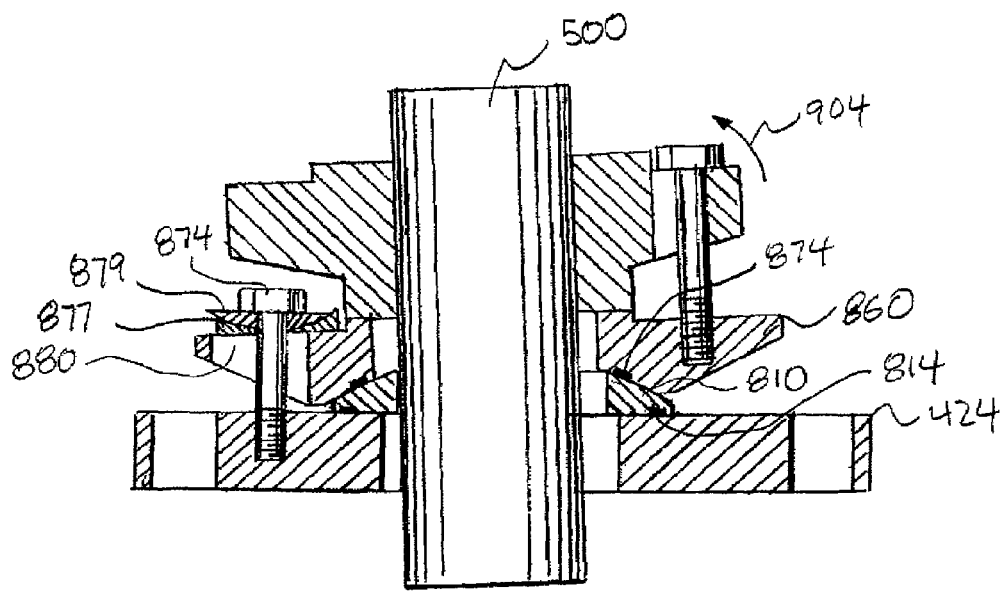
FIG. 26 shows a sectional view of the adjustable seal of FIG. 24 with the shaft angled with respect to the a plate for a roller housing.

FIG. 26 shows a sectional view of adjustable seal 530 with shaft 500 angled with respect to seal 530. Arrow 904 schematically indicates the angled shifting. Cup 860 is shown shifted relative to convex portion 810. Fastener 874 has slid over to absorb the movement indicated by arrow 904. Upper washer 879 has slid relative to lower washer 877. Even so shifted a seal can be made between convex portion 810 and plate 424 through a sealing unit located in groove 814. Additionally, a seal can be made between convex portion 810 and cup 860 through a sealing unit located in groove 872.

Figure 27:
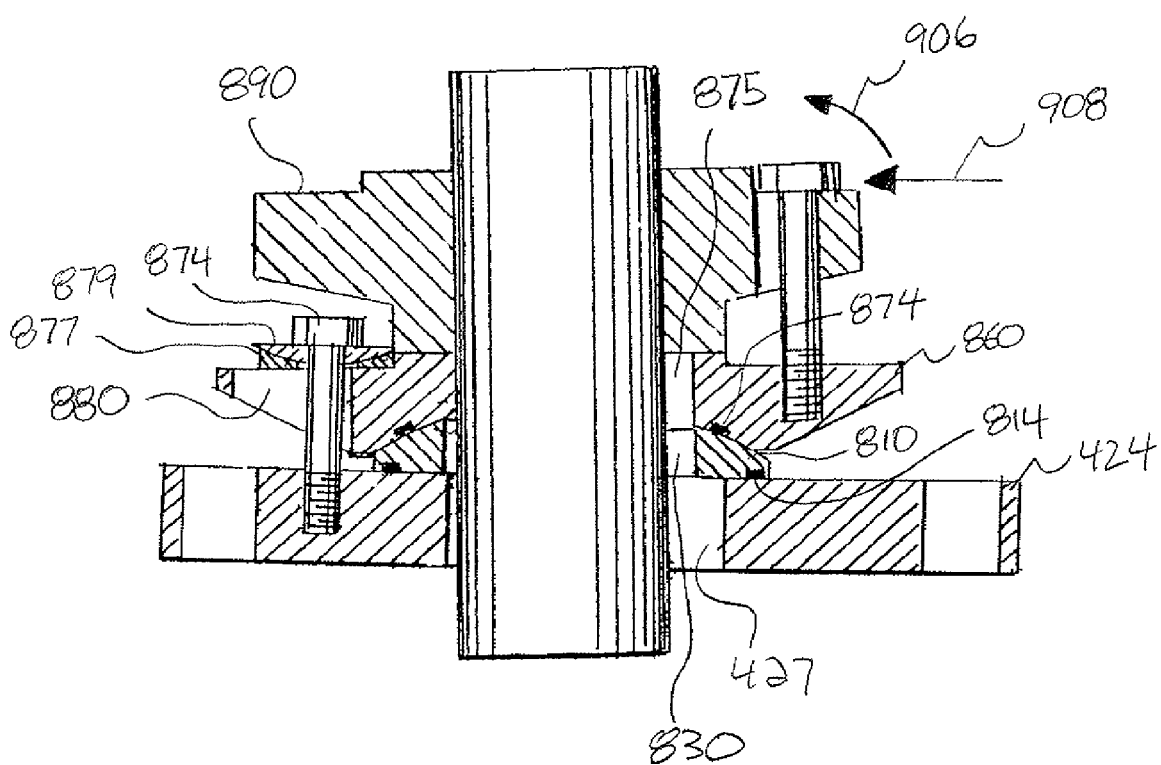
FIG. 27 shows a sectional view of the adjustable seal of FIG. 24 with the shaft offset and angled with respect to a plate for a roller housing.

FIG. 27 shows a sectional view of adjustable seal 530 with shaft 500 offset and angled with respect to seal 530. Arrows 906 and 908 schematically indicate the sliding and angled shifting. Cup 860 is shown shifted relative to convex portion 810. Fastener 874 has slid over to absorb the movement indicated by arrow 904. Upper washer 879 has slid relative to lower washer 877. Even so shifted a seal can be made between convex portion 810 and plate 424 through a sealing unit located in groove 814. Additionally, a seal can be made between convex portion 810 and cup 860 through a sealing unit located in groove 872.

Sealing unit 890 can be mechanical type seal, rope packing type seal, lip seal, or any of the various other shaft seals familiar to those skilled in the art. In addition, sealing unit 890 can be integral with the adjacent part of the sealing device 860, or it can be separable using a fastening system such as threads, clips or other means familiar to one skilled in the art.

Figure 24:
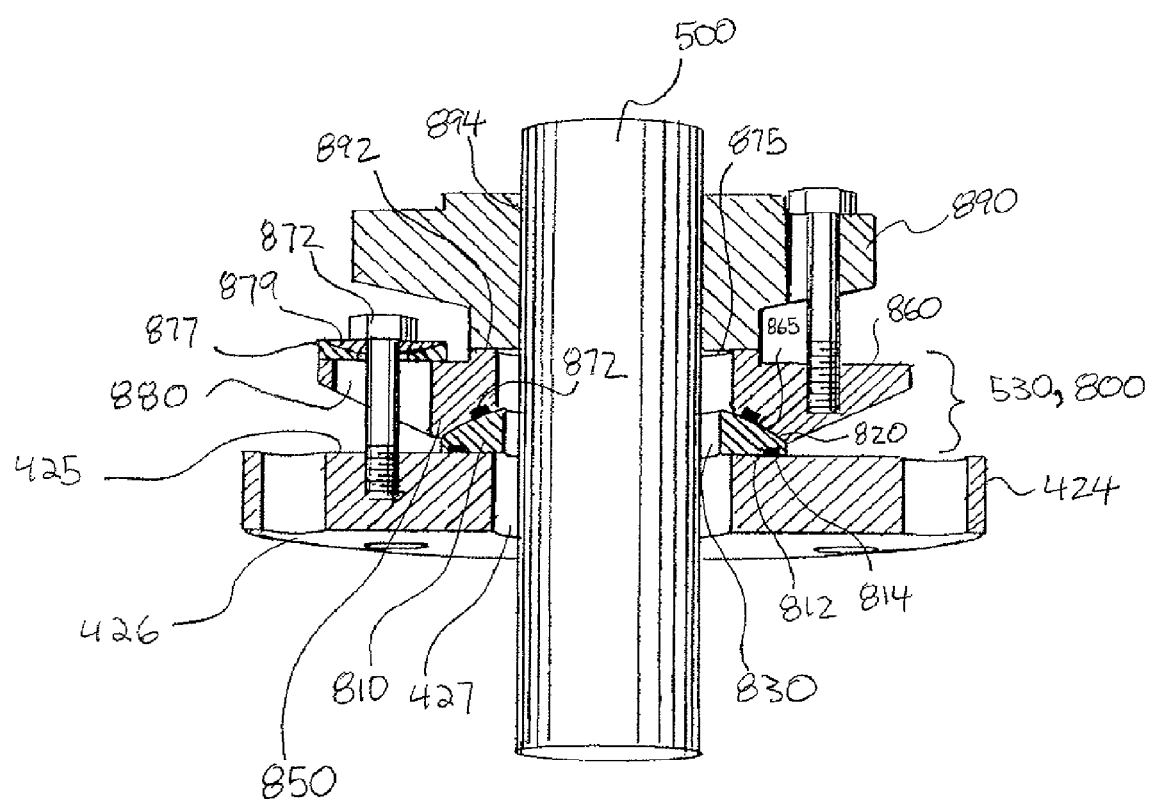
FIG. 24 shows a sectional view of one embodiment of an adjustable seal with the shaft centered with respect to the seal.

Although FIG. 24 shows the preferred arrangement of the concave and convex adjustable or spheriseal parts, the concave component (860) could be placed where the convex component (810) is and the device would be essentially the same, but with slightly different operating characteristics.

The sealing method between the elements of the adjustable seal 530 can use O-rings, gaskets, packing, fine finished gasket free surfaces or other methods familiar to one skilled in the art.

Figure 28:
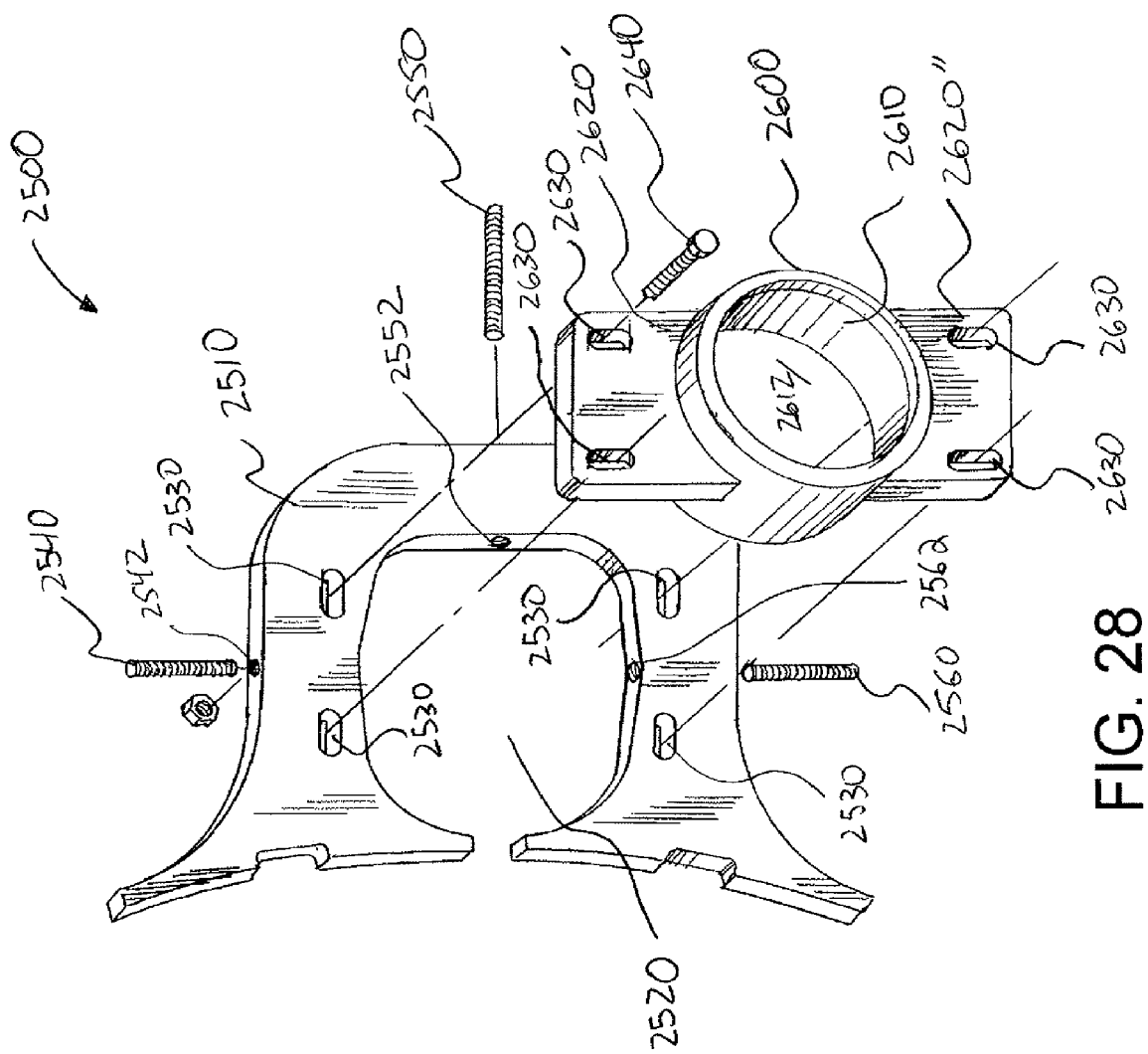
FIG. 28 shows an exploded perspective view of an alternative adjustment apparatus for adjusting the rollers
Figure 29:
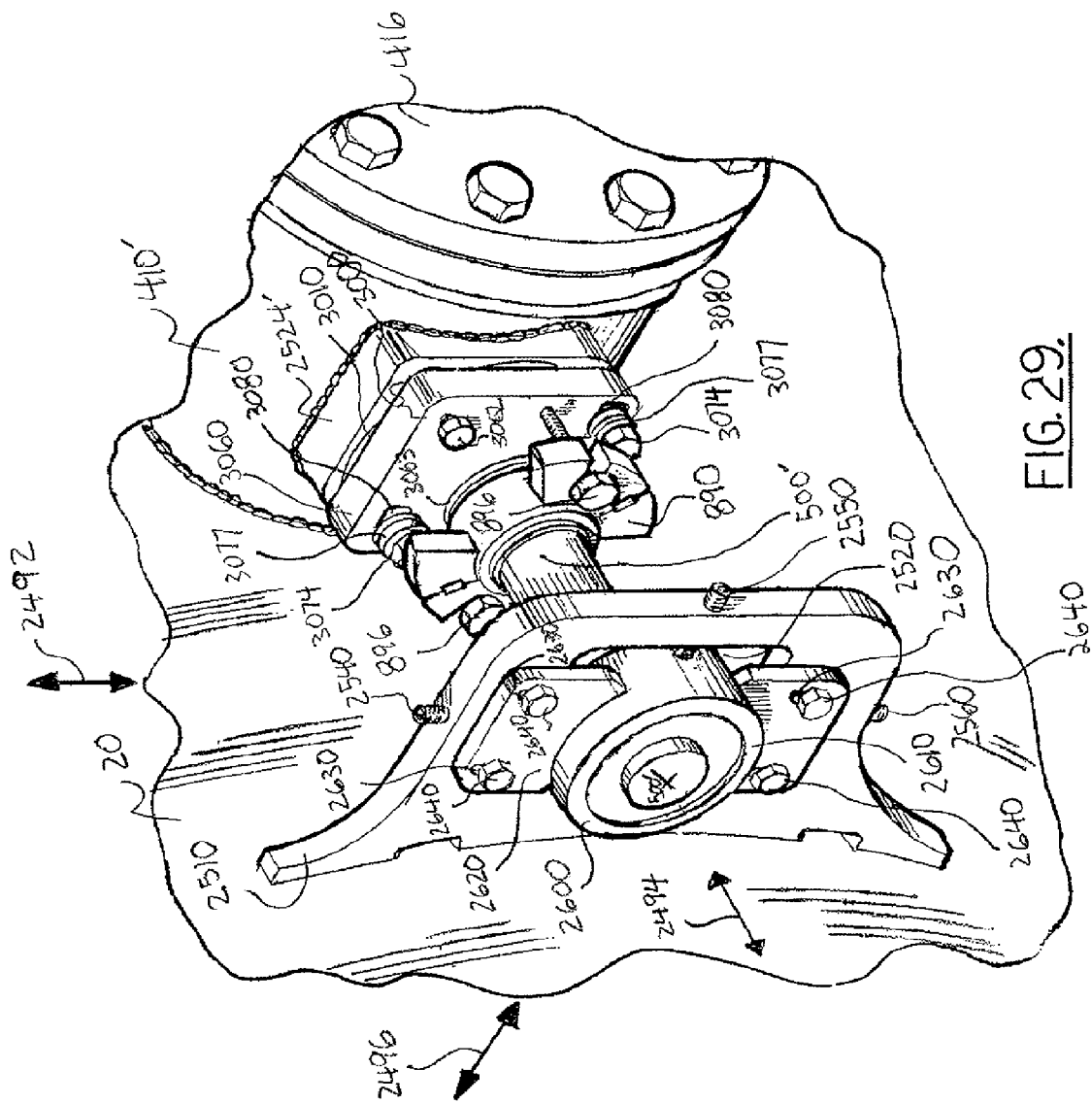
FIG. 29 is a perspective view of a bearing assembly along with the adjustment mechanism of FIG. 28 and an alternative adjustable seal.
Figure 30:
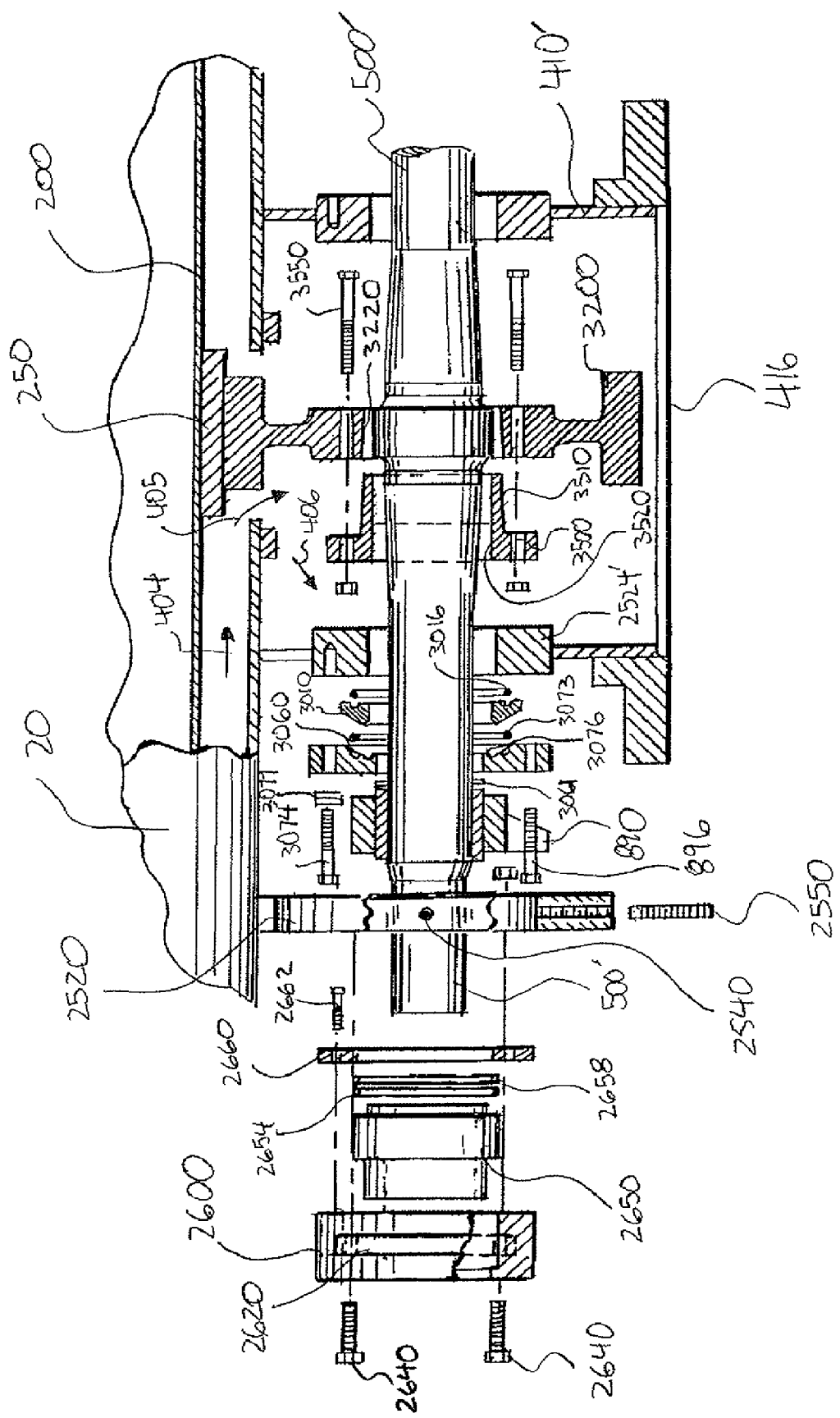
FIG. 30 is a partially exploded sectional view of an alternative roller housing and roller.

FIG. 28 shows an exploded perspective view of an alternative adjustment apparatus 2500 for adjusting the position of a roller (e.g., 400 or 3200) relative to drum 200 (by adjusting the position of shaft 500 relative to drum 200). FIG. 29 is a perspective view of a bearing assembly 2650 along with the adjustment mechanism 2500 and an alternative adjustable seal 3000. Although not shown for clarity, a second adjustment mechanism 2500' and adjustable seal 3000' can be provided on the opposite side of roller housing 410'. FIG. 30 is a partially exploded sectional view of an alternative roller housing 410' and roller 3200. These alternative embodiments will be described in more detail below.

Roller adjustment system 2500 can include adjustment plate 2510 and adjustment collar 2600. Preferably, adjustment collar 2600 can be adjustable relative to adjustment plate in at least two directions, more preferably in three directions. Collar 2600 can also include first and second sections 2620', 2620". Collar 2600 can also include opening 2612, which can house a bearing for shaft 500 or shaft 500'. Adjustment plate 2510 can include large opening 2520 and a plurality of slotted openings 2530 in a spaced apart configuration. Collar 2600 can itself include a plurality of slotted openings 2630 which are preferably not parallel to the plurality of slotted openings 2530 of plate 2510 (an more preferably perpendicular).

The combination of slotted openings 2530 and slotted openings 2630 can allow collar 2600 to be adjusted related to plate 2510 and thereafter locked in an adjusted position by plurality of fasteners 2640. Precision control of adjustment between collar 2600 and plate 2510 can be achieved by use of adjustment means 2540, 2550, and 2560 (e.g., detachable fasteners or threaded fasteners) for adjusting collar 2600 relative to plate 2510. Means 2540, 2550, and 2560 can be threaded into threaded openings 2542, 2552, and 2562 and then positioned to contact collar 2600 at a desired point and/or orientation in space. The desired relative movement between collar 2600 and plate 2510 can be achieved by picking a specific combination of adjustment positions for means 2540, 2550, and/or 2560. For example, movement in the direction of arrow 2492 can be achieved through adjustment of means 2540 and 2560 in the desired location. As another example, movement in the direction of arrow 2496 can be achieved through adjustment of means 2550. Force from the weight of drum 200 will tend to keep collar 2600 touching adjustment means 2550.

Although not shown for clarity, a similar adjustment system 2500' can be included on the opposite side of roller housing 410'. The combination of adjustment system 2500 and 2500' allows shaft 500 or 500' (and roller 400 or 3200) to be properly adjusted relative to drum 200. After the proper adjustment of the roller relative to drum 200 is achieved, then plurality of fasteners 2640 can be used to lock collar 2600 in place relative to plate 2510 (to prevent future movement). Similarly, although not shown, adjustment means 2500' can be locked using a plurality of fasteners 2640' locking collar 2600' in place relative to plate 2510'. By locking in place both adjustment means 2500 and 2500' the roller can be adjusted relative to drum 200 so that the roller smoothly supports drum 200, such as when the roller is correctly adjusted (e.g., exactly perpendicular to drum 200). Adjustment means 2500 is a preferred adjustment system because it reduces the number of moving parts and eliminates the need to use shims when moving in the direction of arrows 2492 and/or 2496. Even after adjustment means 2500 and 2500' have been locked, the precision adjustment means 2540, 2550, and/or 2560 (and precision adjustment means 2540', 2550', and/or 2560' not shown but located on the opposite side of roller housing 410') can be left in place for added support and/or stability of the locking of adjustment means 2500 and/or 2500'. Preferably, both adjusting means 2500 and 2500' are set to adjust shaft 500' and roller 3200 relative to drum 200 before shaft 500' is sealed relative to roller housing 410'. This is because tightening and/or fixing the seals for shaft 500' before proper adjustment of shaft 500' can set up a situation where the seals are moved, broken, and/or compromised when finally adjusting shaft 500'.

Figure 31:
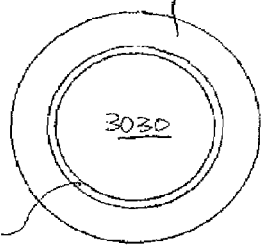
FIGS. 31, 32, and 33 are respectively top, side, and bottom views of an alternative convex piece incorporating a beveled edge.
Figure 32:
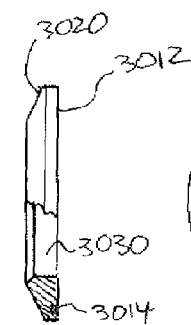
Figure 33:
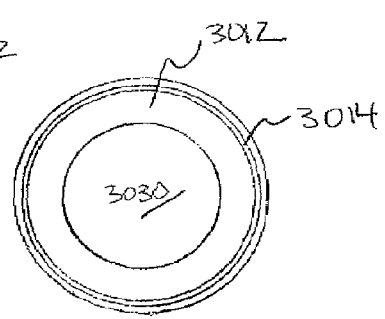
Figures 34, 35, 36:
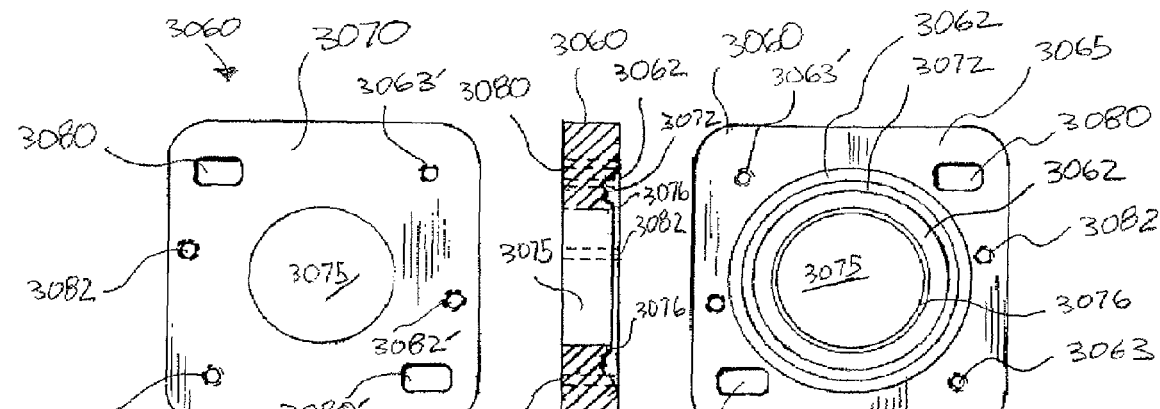
FIGS. 34, 35, and 36 are respectively top, side, and bottom views of an alternative cup incorporating a projecting portion and flat face (as opposed to the tapered face of the cup of FIGS. 21 through 23).

Shown in FIGS. 31 through 36 is an alternative version of an adjustable seal 300 which shows a modified adjustable seal in relation to that disclosed in FIGS. 18 through 23. FIGS. 31 through 33 are respectively top, side, and bottom views of an alternative convex piece 3010 incorporating a beveled edge 3011. FIGS. 34 through 36 are respectively top, side, and bottom views of an alternative cup 3060 incorporating a projecting portion 3076 and flat face (as opposed to the tapered face of the cup 860 of FIGS. 21 through 23). The adjustable seal 3000 disclosed in FIGS. 31 through 36 works similar to the adjustable seal disclosed in FIGS. 18 through 23 and its operation will not again be described. However, projecting portion 3076 of alternative cup 3060 allows the flexibility of restraining the maximum relative movement between convex portion 3010 and cup 3060, which may be important where there is a risk of excessive relative movement compromising the sealing efficacy (such as the risk that o-ring in the cup at least partially moves into the opening through the convex portion—which is a risk where no projecting portion is used with the cup).

Convex portion 3010 can include beveled portion 3011, base 3012, peripheral groove 3014, o-ring for peripheral groove 3014, upper surface 3020, bore 3030.

Deck or cup 3060 can include base 3065, upper surface 3070, concave portion 3062, peripheral groove 3072, o-ring for groove 3073, bore 3075, projecting portion 3076, plurality of openings 3080, and plurality of openings 3082. O-ring 3073 can be slightly larger in diameter than the diameter of peripheral groove 3072.

Alternative adjustable seal 3000 is shown assembled in FIG. 29. Plurality of openings 3080, 3080' allow deck or cup 3060 to be adjustably connected (and also sealably connect convex portion 3010) to roller housing 410' through plate 2524. Plurality of openings 3082,3082' allow mechanical seal 890 to be attached to deck or cup 3060. Deck or cup 3060 can also include a plurality of threaded bores 3063,3063' which accommodate a plurality of adjusting means 3062, 3062' (see FIG. 29) when adjusting deck or cup 3060 relative to the shaft for final connection of mechanical seal 890 to deck or cup 3060.

In another alternative embodiment (shown in FIG. 30) a single piece shaft 500' can be used. This single shaft 500' can include an enlarged area which slides into roller 3200. To connect or fix single shaft 500' relative to roller 3200 an interference fit collar 3500 can be used which are commercially available. Interference collar 3500 can include tapered exterior 3510 which slides and/or fits relative to tapered interior 3220. As interference collar 3500 is pulled into opening of roller 3200 by one or more fasteners, tapered exterior 3510 contacts tapered interior 3220 causing interior bore 3520 to reduce in size until it squeezed against enlarged area of shaft 500' creating an interference or locking fit between roller 3200 and shaft 500'.

It is noted that the preferred order of seal adjustment is first adjusting deck or cup relative to shaft so that it is perpendicular to the shaft (although it does not have to be concentric to the shaft) and then attaching/fixing the deck or cup to the roller housing. After attaching/fixing the deck or cup relative to the roller housing when the deck or cup is perpendicular to the shaft, then the mechanical seal can be attached to the deck or cup. This order allows proper orientation and sealing of deck or cup relative to the mechanical seal as the mechanical seal is perpendicular to the shaft and the deck or cup is perpendicular to the shaft. It has been found that when adjusting the deck or cup relative to the shaft, that one or more precision adjustment means (such one or more threaded bolts) can be used to assist in adjusting the deck or cup. This is because the deck or cup may tend to stick in a particular adjustment position which may require hammering or knocking if a precision adjustment means is not used.

In various embodiments shown for the adjustable seals, three spaced apart fasteners are used to connect or lock the cup portion to the cone portion of the adjustable seals. Additionally three fasteners are used to connect the cone portion to the roller housing. The type, number, and locations of fasteners are not limited but can anything picked by one of ordinary skill in the art. One of ordinary skill in the art can choose more or fewer fasteners for each. For example, two, three, four, five, six, or more fasteners can be used as desired. Using two fasteners decreases the number of fasteners and ease of fastening the various components. Additionally, the fasteners need not be symmetrically spaced, but can be non-symmetrical. Additionally, other fasteners can be used beyond threaded fasteners. Additionally, in one embodiment, the portions of the adjustable seal can be welded or adhered together.

As shown in FIG. 30, spacers or shims 2654 and 2658 can be used to longitudinally lock in place bearing 2650 in collar 2600. In one embodiment, although not shown for clarity, on the other side of roller housing 410', spacers or shims 2654' and 2658' can be used for longitudinally locking bearing 2650'. In one embodiment one of the bearings 2650 or 2650' is set up so that it is an expansion type bearing, which may assist in correctly positioning/adjusting the roller and shaft relative to drum 200. In one embodiment one of the bearings can be an expansion type bearing during adjustment of the roller and converted to a non-expansion type after adjustment of the roller is complete. Converting from expansion to non-expansion can be achieved by picking the number of spacers and/or shims used whereby the longitudinal movement of bearing 2650 and/or 2650' relative to its collar is restricted and/or eliminated.

Devices for monitoring and controlling the process of processor 10, can be included such as water piping, steam piping, vacuum piping, pressure controllers and other needed instruments. Devices of this type should monitor and control the process from a location that is nearer to the point in the process where the reaction is taking place, and not adjacent to or at the opposite end of the injection of additives to the process. Vacuum, in particular, requires that the selected device have considerable strength to keep from collapsing, and this generally equates to massive components, requiring considerable horsepower if such components are to be driven in rotation.

Because of their large size and because of the pressure and vacuum conditions of the process, the end cap 100 would be very difficult to handle manually. Automatic closure device operators 130 that would be affixed to vessel 20 can be used.

Processor 10 can be equipped with piping and controls 2010 for the selective addition of steam, with piping and controls 2040 for the selective addition of water, with suitable valves being utilized in order to control the flow. In one embodiment steam piping and water piping can be combined into a single injection pipe, enabling steam and water to be conducted through the sidewall of vessel 20 and then injected into the open end 210 of drum 200. In one embodiment only steam piping is used.

Figure 37:
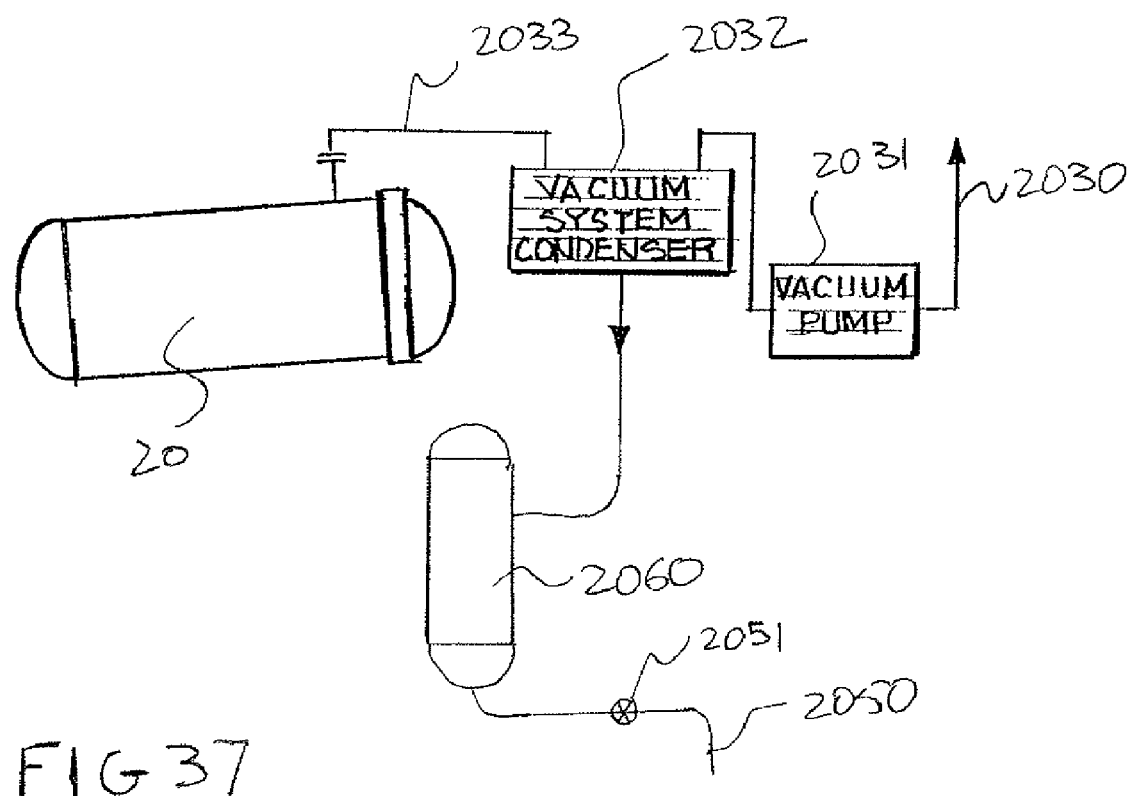
FIG. 37 is a schematic diagram of one example of a vacuum system which can be used in one embodiment.

During one phase of the operation, vacuum can be induced into vessel 20 by a vacuum system. FIG. 37 is a schematic of a vacuum system which can be used. Vacuum system can comprise control 2030, pump 2031, condenser 2032, and vacuum lines 2033. One typical vacuum system which can be used is the type manufactured by Nash Engineering Company of Norwalk, Conn. US or Croll-Reynolds Company, Inc. of Westfield, N.J. US.

Untreated materials can be carried by a suitable conveyor and introduced through inlet opening 210 of drum 200, when end cap 100 has been moved to the open position. In one embodiment inasmuch as waste is typically packaged in bags of various sizes and may also contain an assortment of materials varying in size, shape and density, and which may not necessarily be free flowing, the inlet opening 210 of drum can be large enough and without obstructions so as to allow previously unprocessed waste to be directly introduced into processor 10.

Drum 200 can be rotated in the first rotative direction while materials to be treated are conveyed into drum 200, and, by virtue of the helical flighting 1300,1500 and angle of incline 70 of drum 200, a sufficient amount of the material, though not free flowing, will be loaded into drum 200 for processing. When drum 200 has been filled with a sufficient amount of material to be processed, end cap 100 can be closed and secured by a locking ring 120 as known by those skilled in the art (such as that manufactured by LIBERTY). Several components of the locking ring design utilize wedges, pads, and blocks to provide smooth operation of the door locking system. These components should be made of a material that combines low static friction on steel. Our design utilizes either plastic or bronze, or a combination of these two materials. The plastic can be a plastic material such as Alloy X from Bartlett Engineering of Metairie, La. US or any of a number of other engineered plastics familiar to those knowledgeable in the art such as: Celazole PBI, Duratron X, Fluorosint 50, Kadel E-1130, Kadel E-1140, Kadel EP-3140, PTFE (25% gf), PTFE (25% cf), Rulon LR, Rulon J, Semitron 500, Semitron 520 HR, Techtron PPS, Torlon 5030, Torlon 5530, Ultem 1000, Ultem 2300, Ultem 4001, Vespel SP-1.

In one embodiment substantial quantities of water can be added to the waste to be processed, such that sufficient water is brought into contact with the material in drum 200. In one embodiment moisture can be added to provide a moisture content of between 30% and 90% in the moisture absorbable materials, with approximately 75% being optimum. Drum 200 can ordinarily be rotated in the first rotative direction during the water addition to enhance the contact of the waste materials with the added moisture.

In the first rotative direction, assumed to be clockwise when viewed from the open end of the drum, material to be treated can be intercepted by the directional flighting 1300, 1500 and moved through drum 200 toward back or closed lower end 220 of drum 200. Simultaneously, lifting buckets or upsets 1700 can direct a portion of the material in a separate direction, such as toward inlet end 210 of drum 200 as each of the buckets 1700 comes in contact with the material during the rotation of drum 200. This simultaneous differential movement of materials within drum 200 by the action of helical flightings 1300,1500 and buckets 1700 drum 200 rotation results in a highly advantageous and a very complete agitation of the materials being processed. Because of these actions and the added moisture, the repulping of the pulpable materials of the waste materials is very effectively accomplished.

Alternating Direction of Rotation

In addition, the inner drum can be periodically stopped and the direction of rotation reversed for a portion of or several cycles to reduce the tendency for fibrous or stringy debris to ball up, to increase the agressivness of the conditions inside the drum, to unpack the material from the rear of the drum, or other beneficial reasons apparent to one skilled in the art.

In one embodiment heat can be added to vessel 20 during the processing of materials. In this case, steam may be advantageously added to vessel 20 while drum 200 is being rotated in the first rotative direction. The addition of heat can cause plastics (such as the plastic bags) to become softened and to open and spill their contents into drum 200 while drum 200 is being rotated, thus allowing the materials that were in the bags to be completely agitated and contacted with the added moisture and added heat. Desired pressure can be maintained in vessel 20 by suitable use of the valves of the pressure control system 2020 associated with pressure piping and venting. Valve 2022 controls pipe pressure, and venting valve 2024 controls venting. If desired to add a sterilizing agent, sodium hypochlorite or the like can be added as a liquid or a vapor into drum 200 such as through a steam line, or alternatively a water line. In one embodiment drum 200 can be stopped and reversed one or multiple times during the treatment process.

In one embodiment a temperature of at least 275° F. is maintained for a period of at least 15 minutes at a pressure of approximately 50 psig during the processing of the materials, such as to accomplish the treatment of waste materials. Heat can be added by the injection of steam to attain the required temperature, this being accomplished from the previously described piping, and pressure resulting from the injection of the steam is controlled and maintained by the pressure control system 2020 connected to steam supply piping. Because of added moisture, and very complete agitation, required heat needed to accomplish sterilization of waste materials (such as medical waste) can be better transferred into those materials, such that very effective treatment can be accomplished.

When processing has been completed, steam injection can be shut off and the vacuum control 2030 can be turned on while continuing to rotate drum 200 in the first rotative direction. As a vacuum is induced on vessel 20 and drum 200, moisture can be withdrawn from the processed materials through a vacuum connection and into the vacuum system, and collected for reuse in future processing or for discharge. The amount of water that is added during processing can be absorbed by the moisture absorbable materials that are in the materials to be processed during the processing and should not exist in a pool in drum 200 as a vacuum is being applied. Additionally, as a vacuum is induced in vessel 20, the temperature of the boiling point of any water in drum 200 is reduced and the water is vaporized and withdrawn from the system into the vacuum system. The greater the intensity of the vacuum induced, the greater is the decrease in the boiling point of the water exposed to the vacuum in the system. For instance, at approximately 5 pounds (34.5 kilopascals) of absolute pressure, with 14.7 pounds (101.4 kilopascals) of absolute pressure being equal to the atmospheric pressure and 0 pounds of absolute pressure being a perfect vacuum, water will boil at approximately 162° F. (72° C.) and at approximately 1 pound (6.9 kilopascals) of absolute pressure, water will boil at approximately 102° F. (38.9° C.). Drying techniques such as vacuum evaporation and freeze-drying utilize this phenomenon to accomplish low heat drying.

One embodiment uses high temperatures during the processing and these temperatures are significantly higher than the atmospheric boiling point of water, such that when a vacuum is induced in vessel 20, the vacuum causes a rapid evolution of moisture to vapor and therefore a rapid drying effect of the materials in processor 10. Another benefit of the evaporative effect of moisture loss in this manner is the resulting cooling of the materials that have been processed that they may more easily be handled in subsequent handling operations. Under these conditions, even pooled water will tend to evaporate into vapor and be withdrawn from processor 10.

In one embodiment a vacuum connection is placed on top of vessel 20 in that the evolving vapor, as it is being withdrawn from processor 10, can act as a carrier gas and, by its velocity, can carry light particles with it out of the vessel and into the vacuum system and potentially clog it. By placing a nozzle at the top of vessel 20, gravity will make this action less likely. The installation of such nozzle is also at a point that causes a torturous path to be followed by the vapor, further preventing particles from being carried into the vacuum system in that a change in direction of a carrier gas stream will cause the deposition of particles that are being carried from the gas stream. As the vacuum is induced and the moisture is withdrawn from vessel 20, the processed materials are cooled from the temperature of sterilization to a lower, more manageable temperature for further handling, and from a level of moisture required for effective sterilizing heat penetration to a drier, more manageable moisture level. As is obvious to those skilled in the art, the coolness and the dryness of the processed materials are variables and are dependent on the subsequent requirements of further handling in a particular operation. In this case, a dryness of approximately 20% moisture in the moisture absorbable materials and a corresponding temperature of approximately 200° F. (182° C.) is preferred. If additional cooling needs to be accomplished beyond that attained as a consequence of moisture removal, air can be drawn into the system through a vent connection while the vacuum system continues to operate and, in this manner, additional cooling of the materials can be accomplished.

When the required temperature and dryness are accomplished, the vacuum system can be shut off and rotation of drum 200 stopped. End cap 100 can be opened and drum 200 rotated in the second rotative direction. In the second rotative direction, assuming counterclockwise rotation, the processed materials are intercepted by helical flighting 1300,1500 and directed toward inlet 210 end of drum 200 by the action of helical flighting 1300,1500. In one embodiment, only after the materials have been fully processed, is the rotative direction of drum 200 reversed, so as to enable helical flighting 1300,1500 to discharge the material out of inlet 210 of drum 200 into a suitable discharge system. The processed materials can be discharged from vessel 20 by the combined action of helical flighting 1300,1500 during the rotation of drum 200 in the second rotative direction. Because inlet 210 of drum 200 protrudes beyond the inlet end 50 of vessel 20, the discharged processed materials fall clear of vessel 20.

In one embodiment, by virtue of the repulping of the pulpable materials, the volume of the processed materials can be reduced to approximately ⅓ of its original volume. The rate of discharge of processed materials, as is apparent to those skilled in the art, is dependent on the rate of rotation of drum 200 along with the size and frequency of helical flighting 1300,1500, and these variables are dependent on the amount of material to be processed in a given amount of time.

Drain connection 2050 can be equipped with a suitable valve 2051, which can be opened to enable moisture to be drained from vessel 20 upon excess accumulation thereof.

In one embodiment the processed materials are then directed to screeners for the separation and recovery of recyclable materials and further to compactors or to shredders for the destruction of the remaining materials such as sharps that might be present, that they may safely be disposed of. Other methods and equipment for the separation of component fractions from the processed materials or the further processing of the processed materials as apparent to those skilled in the art and these techniques may also be used for product recovery from the processed materials or for disposal of the residue from the processed materials.

The working fluid in such a vessel does not need to be restricted to just water. Some examples of some fluids used in alternative embodiments include cleaning fluids, reactive gases and liquids, moisture free gases, refrigerated liquids, and solvents.

Such devices can be used for any of a variety of uses including such things as paper pulp, plastic resin drying, coffee bean roasting or treating, food treatment, or rubber processing.

The following is a list of reference numerals:

| LIST FOR REFERENCE NUMERALS | |
|---|---|
| (Part No.) | (Description) |
| 10 | treatment apparatus |
| 20 | vessel |
| 22 | first end |
| 30 | vessel wall |
| 40 | base |
| 50 | inlet |
| 60 | second end |
| 70 | angle of incline |
| 100 | end cap |
| 110 | seal |
| 120 | locking ring |
| 122 | first part |
| 124 | second part |
| 130 | opening mechanism |
| 200 | drum |
| 210 | inlet |
| 220 | second end |
| 230 | wall |
| 250 | roller ring (typically called tire) |
| 260 | arrow indicating rotation around center of drum |
| 300 | drive assembly |
| 310 | drive shaft |
| 314 | bearing |
| 316 | structural member |
| 318 | seal |
| 320 | motor |
| 330 | reduction gearing |
| 340 | chain |
| 350 | sprocket |
| 360 | sprocket |
| 400 | roller |
| 401 | arrows |
| 402 | arrows |
| 403 | arrows |
| 404 | arrow |
| 405 | arrow |
| 406 | arrow |
| 410 | roller housing |
| 412 | base |
| 414 | top |
| 415 | plurality of fasteners |
| 416 | plate |
| 417 | gasket |
| 418 | first opening |
| 420 | plate for first opening |
| 422 | second opening |
| 424 | plate for second opening |
| 425 | upper surface |
| 426 | lower surface |
| 427 | bore for shaft |
| 440 | first bearing |
| 442 | arrows |
| 444 | arrows |
| 450 | shaft |
| 460 | adjustment plate |
| 462 | adjustment means |
| 464 | adjustment means |
| 470 | shim |
| 480 | first adjustable seal |
| 482 | first collar |
| 490 | second bearing |
| 492 | arrows |
| 494 | arrows |
| 500 | shaft |
| 510 | adjustment plate |
| 512 | adjustment means |
| 514 | adjustment means |
| 520 | shim |
| 530 | second adjustable seal |
| 600 | roller |
| 610 | roller housing |
| 612 | base |
| 614 | top |
| 616 | plate |
| 618 | first opening |
| 620 | plate for first opening |
| 622 | second opening |
| 624 | plate for second opening |
| 640 | first bearing |
| 650 | shaft |
| 660 | adjustment plate |
| 670 | shim |
| 680 | first adjustable seal |
| 690 | second bearing |
| 700 | shaft |
| 710 | adjustment plate |
| 720 | shim |
| 730 | second adjustable seal |
| 800 | adjustable seal |
| 810 | convex portion |
| 812 | base |
| 814 | peripheral groove |
| 816 | o-ring for peripheral groove |
| 820 | upper surface |
| 830 | bore |
| 860 | cup |
| 865 | base |
| 870 | upper surface |
| 871 | raised area |
| 872 | groove |
| 873 | o-ring for groove |
| 874 | fastener |
| 875 | bore |
| 877 | lower part of washer |
| 878 | bore through lower washer |
| 879 | upper part of washer |
| 880 | bore |
| 882 | opening |
| 890 | winged collar mechanical seal for shaft |
| 891 | gasket |
| 892 | base |
| 894 | bore |
| 896 | plurality of fasteners |
| 900 | arrow |
| 902 | arrow |
| 904 | arrow |
| 906 | arrow |
| 908 | arrow |
| 909 | arrow |
| 910 | arrows |
| 920 | arrow |

LIST FOR REFERENCE NUMERALS -continued

| (Part No.) | (Description) |
|---|---|
| 950 | angle of rotation |
| 1300 | first helix |
| 1310 | first end |
| 1320 | second end |
| 1330 | height |
| 1340 | length |
| 1350 | pitch |
| 1360 | base |
| 1370 | top |
| 1500 | second helix |
| 1510 | first end |
| 1520 | second end |
| 1530 | height |
| 1540 | length |
| 1550 | pitch |
| 1560 | base |
| 1570 | top |
| 1700 | bucket |
| 1710 | base |
| 1720 | tip |
| 1730 | first section |
| 1732 | angle |
| 1733 | angle |
| 1734 | angle |
| 1735 | transition |
| 1740 | second section |
| 1750 | decreasing portion |
| 1800 | cutting bucket |
| 1802 | arrow |
| 1810 | base |
| 1820 | first side |
| 1830 | second side |
| 1840 | plurality of projections |
| 1842 | object |
| 1870 | plurality of projections |
| 1872 | projection |
| 1874 | projection |
| 1876 | projection |
| 1878 | projection |
| 1880 | projection |
| 1900 | hook |
| 1902 | arrow |
| 1910 | hook |
| 1920 | hook |
| 1930 | hook |
| 1940 | item |
| 1942 | item |
| 1944 | item |
| 1946 | material to be treated |
| 2000 | control panel |
| 2010 | steam control valve |
| 2015 | steam supply piping |
| 2020 | pressure control valve |
| 2022 | pressure relief valve |
| 2024 | main vessel vent valve |
| 2026 | safety interlock mechanism |
| 2030 | non-condensables vent |
| 2031 | vacuum pump or vacuum device |
| 2032 | vacuum system condenser (or pre condenser) |
| 2033 | vacuum line |
| 2034 | after-condenser |
| 2035 | vapor valve |
| 2037 | vacuum device control valve |
| 2040 | cooling water control |
| 2045 | process water control |
| 2050 | drain |
| 2051 | drain valve |
| 2060 | condensed water collection tank |
| 2070 | non-condensables vent pipe |
| 2492 | arrow |
| 2494 | arrow |
| 2496 | arrow |
| 2500 | roller adjustment system |
| 2510 | adjustment plate |
| 2520 | opening for adjustment plate |
| 2530 | plurality of slotted openings |
| 2540 | adjustment means |
| 2542 | threaded opening |
| 2550 | adjustment means |
| 2552 | threaded opening |
| 2560 | adjustment means |
| 2562 | threaded opening |
| 2600 | adjustment collar |
| 2610 | first section of adjustment collar |
| 2612 | opening in first section of adjustment collar |
| 2620 | second section of adjustment collar |
| 2630 | plurality of slotted openings |
| 2640 | fastener |
| 2650 | bearing |
| 2654 | shim |
| 2658 | shim |
| 2660 | containment plate |
| 2662 | plurality of fasteners |
| 3000 | adjustable seal |
| 3010 | convex portion |
| 3011 | beveled portion |
| 3012 | base |
| 3014 | peripheral groove |
| 3016 | o-ring for peripheral groove |
| 3020 | upper surface |
| 3030 | bore |
| 3060 | deck or cup |
| 3061 | gasket |
| 3062 | adjustment means |
| 3063 | bore for adjustment means (which can be threaded) |
| 3062 | concave portion |
| 3065 | base |
| 3070 | upper surface |
| 3071 | raised area |
| 3072 | groove |
| 3073 | o-ring for groove |
| 3074 | fastener |
| 3075 | bore |
| 3076 | protruding section of bore |
| 3077 | slidable washers for adjusting |
| 3080 | bore |
| 3082 | opening |
| 3084 | opening |
| 3200 | roller |
| 3220 | tapered bore |
| 3500 | interference fitting or collar |
| 3510 | tapered outer portion |
| 3520 | internal bore |
| 3550 | plurality of fasteners |

One embodiment includes a method and apparatus processing materials including medical waste, municipal waste, along with other wastes, and processing materials; the apparatus comprising an elongate pressure vessel of generally cylindrical configuration having an inlet end, and an end cap for the inlet. An elongate drum of generally cylindrical configuration can be mounted in the vessel for rotation about its longitudinal axis, which drum can be selectively driven in either rotative direction. The longitudinal axis of the drum can be inclined relative to the horizontal, placing the inlet end at a higher elevation than the opposite end. A helically configured member can be included along the interior perimeter of the drum, such that during rotation of the drum in a first rotative direction, the helically configured member tends to move the material to be treated in a direction away from the inlet end, and during rotation of the drum in the second rotative direction, the helically configured member tends to move the material toward the inlet end. The helically configured member can be used in conjunction with a plurality of upsets or buckets that tend to mix and break up the materials to be treated. Moisture and heat can be used to aid the processing of the waste, such as by the addition of steam. Discharge of the fully processed materials can be made when the drum is being rotated in the second rotative direction, after the end cap has been opened.

In one embodiment the method separates component fractions from paper-containing and plastic-containing waste materials. This embodiment can accepts materials of widely varying characteristics such as paper, plastics, glass, metal, food wastes and other materials to be inserted en masse into the drum. Intimate contact of materials with moisture and heat can be accomplished, thus effecting repulping of paper materials. The repulped materials, as a result of directional tumbling, are dispersed throughout the vessel. Because of the repulping of the pulpable materials, size reduction of randomly large and odd-shaped repulpable material is accomplished. By virtue of the size reduction of the large and odd-shaped pulpable materials, the non-pulpable components are freed of the particle shapes and surfaces that affect separation. The pulping of the pulpable materials increases the bulk density of those materials, further enhancing their separation from the additional components. The recovered repulped product can be suitable for recycling in the paper industry; for combustion as a high quality fuel, or for use as a feedstock for conversion into chemicals. The recovered non-pulpable materials such as plastics, glass, metals, aluminum and other materials can be suitable for recycling into their producer industries; as feedstock raw materials for additional manufacturing of products; or any or all of these materials can be disposed of in a sanitary landfill as is the commonly accepted practice.

All measurements disclosed herein are at standard temperature and pressure, at sea level on Earth, unless indicated otherwise. All materials used or intended to be used in a human being are biocompatible, unless indicated otherwise.

It will be understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only; the scope of the present invention is to be limited only by the following claims.

The invention claimed is:

1. A treatment vessel comprising:
   (a) a shell;
   (b) a drum, the drum being rotatively connected to the shell;
   (c) wherein pressure and heat can be added to the drum; and
   (d) wherein the drum is supported by at least one bearing, the bearing being sealed from the pressure and heat added to the drum, and wherein the at least one bearing rotatively supports a first roller and first shaft, the at least one bearing being sealed by a first seal, the first seal allowing a combination of both angular and offset movement of the first shaft.

2. The treatment vessel of claim 1, further comprising a second bearing rotatively supporting the first roller and first shaft, the second bearing being sealed by a second seal, the second seal allowing a combination of both angular and offset movement of the first shaft.

3. The treatment vessel of claim 1, further comprising a second bearing angularly spaced apart from the bearing, the second bearing being sealed from the pressure and heat added to the drum.

4. The treatment vessel of claim 3, wherein the at least one bearing rotatively supports a first roller and first shaft, the at least one bearing being sealed by a first seal, the first seal allowing a combination of both angular and offset movement of the first shaft, and wherein the second bearing rotatively supports a second roller and second shaft, and the second bearing being sealed by a second seal, the second seal allowing a combination of both angular and offset movement of the second shaft.

5. The treatment vessel of claim 1, wherein the drum includes a helix, the helix tending to move material located in the drum in one direction during rotation in a first direction and move material in the opposite direction during rotation in a second direction, the helix including a plurality of buckets attached to the helix.

6. The treatment vessel of claim 5, wherein each bucket includes a base attached to the helix and a second end which is angularly offset from the base.

7. The treatment vessel of claim 6, wherein the second end includes a decreasing portion.

8. The treatment vessel of claim 6, wherein the base is substantially perpendicular to the helix.

9. The treatment vessel of claim 5, wherein three buckets are used.

10. The treatment vessel of claim 5, wherein the buckets are located in the rear third of the drum.

11. The treatment vessel of claim 1, wherein the drum includes a helix, the helix tending to move material located in the drum in one direction during rotation in a first direction and move material in the opposite direction during rotation in a second direction, the drum including a plurality of buckets, and the helix includes a plurality of spikes.

12. The treatment vessel of claim 11, wherein each bucket includes a plurality of spikes.

13. The treatment vessel of claim 1, wherein the drum includes a helix, the helix tending to move material located in the drum in one direction during rotation in a first direction and move material in the opposite direction during rotation in a second direction, and the helix includes a plurality of spikes.

14. The treatment vessel of claim 1, wherein the drum includes a helix, the helix tending to move material located in the drum in one direction during rotation in a first direction and move material in the opposite direction during rotation in a second direction, and the helix includes a plurality of hooks.

15. The treatment vessel of claim 14, wherein a plurality of spikes are pointed substantially in the first direction of rotation.

16. A treatment vessel comprising:
   (a) a shell;
   (b) a drum, the drum being rotatively connected to the shell;
   (c) wherein pressure and heat can be added to the drum;
   (d) wherein the drum is supported by at least one bearing, the bearing being sealed from the pressure and heat added to the drum; and
   (e) wherein the drum includes a helix, the helix tending to move material located in the drum in one direction during rotation in a first direction and move material in the opposite direction during rotation in a second direction, the helix including a plurality of buckets attached to the helix.

17. The treatment vessel of claim 16, wherein the at least one bearing rotating supports a first roller and first shaft, the at least one bearing being sealed by a first seal, the first seal allowing a combination of both angular and offset movement of the first shaft.

18. The treatment vessel of claim 17, further comprising a second bearing rotatively supporting the first roller and first shaft, the second bearing being sealed by a second seal, the second seal allowing a combination of both angular and offset movement of the first shaft.

19. The treatment vessel of claim 16, further comprising a second bearing angularly spaced apart from the bearing, the second bearing being sealed from the pressure and heat added to the drum.

20. The treatment vessel of claim 19, wherein the at least one bearing rotatively supports a first roller and first shaft, the at least one bearing being sealed by a first seal, the first seal allowing a combination of both angular and offset movement of the first shaft, and wherein the second bearing rotatively supports a second roller and second shaft, and the second bearing being sealed by a second seal, the second seal allowing a combination of both angular and offset movement of the second shaft.

21. The treatment vessel of claim 16, wherein each bucket includes a base attached to the helix and a second end which is angularly offset from the base.

22. The treatment vessel of claim 21, wherein the second end includes a decreasing portion.

23. The treatment vessel of claim 21, wherein the base is substantially perpendicular to the helix.

24. The treatment vessel of claim 21, wherein three buckets are used.

25. The treatment vessel of claim 21, wherein the buckets are located in the rear third of the drum.

26. The treatment vessel of claim 16, wherein each bucket includes a plurality of spikes.

27. The treatment vessel of claim 16, wherein the drum includes a helix, the helix tending to move material located in the drum in one direction during rotation in a first direction and move material in the opposite direction during rotation in a second direction, and the helix includes a plurality of spikes.

28. The treatment vessel of claim 27, wherein the plurality of spikes are pointed substantially in the first direction of rotation.

29. A treatment vessel comprising:
(a) a shell;
(b) a drum, the drum being rotatively connected to the shell;
(c) wherein pressure and heat can be added to the drum;
(d) wherein the drum is supported by at least one bearing, the bearing being sealed from the pressure and heat added to the drum; and
(e) wherein the drum includes a helix, the helix tending to move material located in the drum in one direction during rotation in a first direction and move material in the opposite direction during rotation in a second direction, the drum including a plurality of buckets, and the helix includes a plurality of spikes.

30. A treatment vessel comprising:
(a) a shell;
(b) a drum, the drum being rotatively connected to the shell;
(c) wherein pressure and heat can be added to the drum;
(d) wherein the drum is supported by at least one bearing, the bearing being sealed from the pressure and heat added to the drum; and
(e) wherein the drum includes a helix, the helix tending to move material located in the drum in one direction during rotation in a first direction and move material in the opposite direction during rotation in a second direction, and the helix includes a plurality of hooks.

* * * * *